US006071716A

United States Patent [19]
Freeman et al.

[11] Patent Number: 6,071,716
[45] Date of Patent: Jun. 6, 2000

[54] DNA ENCODING, B7, A NEW MEMBER OF THE IG SUPERFAMILY WITH UNIQUE EXPRESSION ON ACTIVATED AND NEOPLASTIC B CELLS

[75] Inventors: Gordon J. Freeman, Brookline; Arnold S. Freedman; Lee M. Nadler, both of Newton, all of Mass.

[73] Assignee: Dana-Farber Cancer Institute, Boston, Mass.

[21] Appl. No.: 08/153,262

[22] Filed: Nov. 15, 1993

Related U.S. Application Data

[63] Continuation of application No. 07/751,306, Aug. 28, 1991, abandoned, which is a continuation-in-part of application No. 07/591,300, Oct. 1, 1990, abandoned.

[51] Int. Cl.$^7$ .................................................. C12N 15/00
[52] U.S. Cl. ..................... 435/69.1; 435/320.1; 435/325; 435/252.3; 435/254.1; 530/350; 536/23.5
[58] Field of Search ............................... 435/172.3, 69.1, 435/320.1, 325, 252.3, 254.1; 536/23.1, 23.5; 530/350

[56] References Cited

U.S. PATENT DOCUMENTS

| 4,692,405 | 9/1987 | Freedman et al. | 435/7 |
| 5,580,756 | 12/1996 | Linsley | 435/69.7 |

FOREIGN PATENT DOCUMENTS

| 0330191 | 8/1989 | European Pat. Off. . |
| 9005541 | 5/1990 | WIPO . |

OTHER PUBLICATIONS

George et al., Macromolecular sequencing and synthesis, Alan Riss , p. 127–149, 1988.
Freeman et al., J.Exp.Med. 174:625–631, Sep. 1991.
Wahl & Meth in Enz 152: 399, 1987.
Treiger et al J of Immunol 136(11): 4099, 1986.
Young et al PNAS 80: 1194, 1983.
Webster's Dictionary, p. 781.
Young, Richard A, and Ronald W. Davis, "Gene Isolation with λgt11 System" (1991), *Methods in Enzymology* 194:230.
Young, Richard A. and Ronald W. Davis, "Immunoscreening λgt11 Recombinant DNA Expression Libraries", *Genetic Engineering—Principles and Methods*, 1985 Plenum Press, New York, vol. 7, pp. 29–41.
Mierendorf, Robert C. et al., "Gene Isolation by Screening λgt11 Libraries with Antibodies" (1987), *Methods in Enzymology* 152:458.
Helfman, David M. and Stephen H. Hughes, "Use of Antibodies to Screen cDNA Expression Libraries Prepared in Plsmid Vectors" (1987), *Methods in Enzymology* 152:451.
Alan R. Kimmel, "Selection of Clones from Libraries: Overview" (1987), *Methods in Enzymology* 152:393.
Freeman et al, "B7, a New Member of the Ig Superfamily with Unique Expression on Activated and Neoplastic B Cells", *The Journal of Immunology*, 143:2714–2722 (Oct. 15, 1989).

Freeman et al, "Molecular cloning of the B–cell–restricted activation antigen B7 identifies a new member of the immunoglobulin gene family", *Leukocyte Typing IV* (ed. W. Knapp et al.) Oxford Univ. Press, Oxford, UK, (Feb. 1990) pp. 141–142.
Freemand et al, "B7, A b Cell–Restricted Antigen that Identifies Preactivated B Cells", The Journal of Immunology, 139:3260–3267.
Seed and Aruffo, "Molecular Cloning of the CD2 antigen, the T–cell erythrocyte receptor, by a rapid immunoselection procedure", *Proc. Natl. Acad. Sci.*, 84:3365–3369 (May 1987).
Seed and Aruffo, "Molecular Cloning of CD28 cDNA by a high efficiency COS cell expression system", Proc. Natl. Acad. Sci., 84:8573–8577 (Dec. 1987).
Clark et al, "Human B cell and B cell blast–associated surface molecules defined with monoclonal antibodies", *Leukocyte Typing* (ed. A. Bernard, L. Boumsell, J. Dausset, C. Milstein, S.F. Schlossman) Springer–Verlag, Berlin, FRD, pp. 339–346 (1984).
Clark et al, "polypeptides on Human B Lymphocytes Associated with Cell Activation", Human Immunology vol. 16, pp. 100–113, (1986).
Clark et al, "Structure, Function, and Genetics of Human B Cell–Associated Surface Molecules", *Advances In Cancer Research*, vol. 52, pp. 81–149 (1989).
Ehlin–Henriksson et al, "Studies on the B Lymphoblast Antigen No. 1 (BB–1) on a Series of Burkitt Lymphoma Lines Differing in the Expression of the EBV/C3 Receptor Complex", *The Journal of Immunology*, vol. 130, No. 5, pp. 2448–2451, (May 1983).
June et al, "Role of the CD28 receptor in T–cell activation", Immunology Today, vol. 11, No. 6, pp. 211–216 (1990).
Katz et al, "Chromosome mapping of cell membrane antigens expressed on activated B cells", Eur. J. Immunol., vol. 15, pp. 103–106 (1985).
Schwartz, "A Cell Culture Model for T Lymphocyte Clonal Anergy", *Science*, vol. 248, pp. 1349–1356, (Jun. 15, 1990).
Seed, "An LFA–3 cDNA encodes a phospholipid–linked membrane protein homologous to its receptor CD2", *Nature* 329:840–842 (1987).

(List continued on next page.)

*Primary Examiner*—Lorraine Spector
*Assistant Examiner*—Eliane Lazar-Wesley
*Attorney, Agent, or Firm*—Lahive & Cockfield, LLP; Amy E. Mandragouras, Esq.; Megan E. Williams

[57] ABSTRACT

Isolated nucleic acid molecules encoding a B cell activation antigen, B7, are provided. In one embodiment, the nucleic acid molecules are DNA sequences. The DNA sequences of the invention can be integrated into various expression vectors, which in turn can direct the synthesis of the corresponding proteins or peptides in a variety of hosts, particularly eukaryotic cells, such as mammalian and insect cell culture. Also provided are host cells transformed to produce proteins or peptides encoded by the DNA molecules of the present invention and purified proteins and peptides which comprise at least a portion of the B cell activation antigen. The proteins and peptides comprise at least a portion of the mature form of the B7 activation antigen and preferably comprise a soluble form of the B7 protein.

38 Claims, 8 Drawing Sheets

OTHER PUBLICATIONS

Linsley et al, "The T Cell Antigen, CD28, Mediates Adhesion with B Cells by Interacting with the Activation Antigen, B7/BB–1", *Proc. Natl. Acad. Sci.*, 87:5031–5035 (Jul. 1990).

Gimmi et al, "B7 Provides a Costimulatory Signal Which Induces T Cells to Proliferate and Secrete IL–2", *Proc. Natl. Acad. Sci.*, 88:6575–6579 (Aug. 1991).

Koulova et al, "The CD28 Ligand B7/BB1 Provides Costimulatory Signal for Alloactivation of CD4$^+$ T Cells", *J. Exp. med.*, 173:759–762 (Mar. 1991).

Linsley et al, "Binding of the B Cell Acivation Antigen B7 to CD28 Costimulates T Cell Proliferation and Interleukin 2 mRNA Accumulation", *J. Exp. Med.*, 173:721–730 (Mar. 1991).

Damle et al, "Direct helper T cell–induced B cell differentiation involves interaction between T cell antigen CD28 and B cell acivation antigen B7", *Eur. J. Immunol.*, 21:1277–1282 (1991).

```
          ---------------------signal-------------------------
M  -37  Met Ala Cys Asn Cys Gln Leu Met Gln Asp Thr Pro Leu Leu Lys Phe  -22
H  -34                  Met Gly His Thr Arg Arg Gln Gly Thr Ser Pro Ser Lys Cys  -21

-21  Pro Cys Pro Arg Leu Ile Leu Leu Phe Val Leu Leu Ile Arg Leu Ser   -6
   -20  Pro Tyr Leu Asn Phe Gln Leu Leu     Val Leu Ala Gly Leu Ser       -6

-5  Gln Val Ser Ser Asp Val Asp Glu Gln Leu Ser Lys Ser Val Lys Asp   11
    -5  His Phe Cys Ser Gly Val         Ile His Val Thr Lys Glu Val Lys Glu  10
                              1

12  Lys Val Leu Leu Pro Cys Arg Tyr Asn Ser Pro His Glu Asp Glu Ser   27
    11  Val Ala Thr Leu Ser Cys Gly His Asn Val Ser Val Glu Glu Leu Ala   26
                                                *
```

FIGURE 4A

| 28 | Glu | Asp | Arg | Ile | Tyr | Trp | Gln | Lys | His | Asp | Lys | Val | Leu | Ser | Val | 43 |
| 27 | Gln | Thr | Arg | Ile | Tyr | Trp | Gln | Lys | Glu | Lys | Lys | Val | Met | Val | Leu | — | Leu | Thr | Met | 42 |

| 44 | Ile | Ala | Gly | Lys | Leu | Lys | Val | Trp | Pro | Glu | Tyr | Lys | Asn | Arg | Thr | * | Leu | 59 |
| 43 | Met | Ser | Gly | Asp | Met | Asn | Ile | Trp | Pro | Glu | Tyr | Lys | Asn | — | Arg | — | * | Thr | Ile | 58 |

| 60 | Tyr | Asp | Asn | Thr | * | Thr | Tyr | Ser | Leu | Ile | Ile | Leu | Gly | Val | Leu | 74 |
| 59 | Phe | Asp | Ile | Thr | Asn | Asn | Leu | * | Ser | Ile | Val | Ile | Leu | Ala | Leu | Arg | Pro | 74 |

| 75 | Ser | Asp | Arg | Gly | Thr | Tyr | Ser | Cys | Val | Val | Gln | Lys | Lys | Glu | Arg | Gly | 90 |
| 75 | Ser | Asp | Glu | Gly | Thr | Tyr | Glu | Cys | Val | Val | Leu | Lys | Tyr | Glu | Lys | Pro | Asp | 90 |

FIGURE 4B

| 91  | Thr | Tyr | Gly | Val | Lys | His | Leu | Ala | Leu | Val | Lys | Leu | Ser | Ile | Lys | Ala | 106 |
| 91  | Ala | Phe | Lys | Arg | Glu | His | Leu | Ala | Glu | Val | Thr | Leu | Ser | Val | Lys | Ala | 106 |
| 107 | Asp | Phe | Ser | Thr | Pro | Asn | Ile | Thr | Glu | Ser | Gly | Asn | * Pro | Ser | Ala | Asp | 122 |
| 107 | Asp | Phe | Pro | Thr | Pro | Ser | Ile | Ser | Asp | Phe | Glu | Ile | Pro | Thr | Ser | Asn | 122 |
| 123 | Thr | Lys | Arg | Ile | Thr | Cys | Phe | Ala | Ser | Gly | Gly | Phe | Pro | Lys | Pro | Arg | 138 |
| 123 | Ile | Arg | Arg | Ile | Ile | Cys | Ser | Thr | Ser | Gly | Gly | Phe | Pro | Glu | Pro | His | 138 |
| 139 | Phe | Ser | Trp | Leu | Glu | Asn | Gly | Arg | Glu | Leu | Pro | Gly | Ile | Asn | * Thr | Thr | 154 |
| 139 | Leu | Ser | Trp | Leu | Glu | Asn | Gly | Glu | Glu | Leu | Asn | Ala | Ile | Asn | * Thr | Thr | 154 |

FIGURE 4C

| 155 | Ile | Ser | Gln | Asp | Pro | Glu | Ser | Glu | Leu | Tyr | Thr | Ile | Ser | Ser | Gln | Leu | 170 |
|-----|-----|-----|-----|-----|-----|-----|-----|-----|-----|-----|-----|-----|-----|-----|-----|-----|-----|
| 155 | Val | Ser | Gln | Asp | Pro | Glu | Thr | Glu | Leu | Tyr | Ala | Val | Ser | Ser | Lys | Leu | 170 |

| 171 | Asp | Phe | Asn | Thr | Thr | Arg | Asn | His | Thr | Ile | Lys | Cys | Leu | Ile | Lys | Tyr | 186 |
|-----|-----|-----|-----|-----|-----|-----|-----|-----|-----|-----|-----|-----|-----|-----|-----|-----|-----|
|     |  *  |     |     |  *  |     |     |     |  *  |     |     |     |     |     |     |     |     |     |
| 171 | Asp | Phe | Asn | Met | Thr | Thr | Asn | His | Ser | Phe | Met | Cys | Leu | Ile | Lys | Tyr | 186 |

| 187 | Gly | Asp | Ala | His | Val | Ser | Glu | Asp | Phe | Thr | Trp | Glu | Lys | Pro | Pro | Glu | 202 |
|-----|-----|-----|-----|-----|-----|-----|-----|-----|-----|-----|-----|-----|-----|-----|-----|-----|-----|
| 187 | Gly | His | Leu | Arg | Val | Asn | Gln | Thr | Phe | Asn | Trp | Asn | Thr | Thr | Lys | Gln | 202 |
|     |     |     |     |     |     |     |  *  |     |     |     |     |     |  *  |     |     |     |     |

Transmembrane

| 203 | Asp | Pro | Pro | Ser | Lys | Asn | Thr | Leu | Val | Leu | Phe | Gly | Ala | Gly | Phe | 218 |
|-----|-----|-----|-----|-----|-----|-----|-----|-----|-----|-----|-----|-----|-----|-----|-----|-----|
| 203 | Glu | His | Phe | Pro | Asp | Asn | Leu | Leu | Pro | Ser | Trp | Ala | Ile | Thr | Leu | 218 |

FIGURE 4D

```
M 219  Gly Ala Val Ile Thr Val Val Val Ile Ile Lys Cys Phe 234
           |       |           |   |
H 219  Ile Ser Val Asn Gly Ile Phe Val Cys Leu Thr Tyr Cys Phe 233

------------------------Cytoplasmic------------------------
M 235  Cys Lys his Arg Ser Cys Phe Arg Arg Asn Glu      Ala Ser Arg Glu 249
           ---*---                     |   |                 |
H 234  Ala Pro Arg Cys Arg Glu Arg Arg Asn Glu      Arg Leu Arg Arg Glu 249

M 250  Thr Asn Ser Leu Thr Phe Gly Pro Glu Glu Ala Leu Ala Glu Gln
                  ---*---
H 250  Ser Val Arg Pro Val* 254

M      Thr Val Phe Leu* 269
```

FIGURE 4E

DNA ENCODING, B7, A NEW MEMBER OF THE IG SUPERFAMILY WITH UNIQUE EXPRESSION ON ACTIVATED AND NEOPLASTIC B CELLS

This application is a continuation of application Ser. No. 07/751,306, filed on Aug. 28, 1991, now abandoned which is a continuation-in-part of U.S. Ser. No. 07/591,300 Filed on Oct. 1, 1990, now abandoned.

GOVERNMENT RIGHTS TO INVENTION

This invention was made with Government support under National Institutes of Health Grants CA-34183 and CA-40216 and Public Health Services Grant 5KO8 CA-01105 awarded by the National Cancer Institute, Department of Health and Human Services. The Government therefore has certain rights in this invention.

FIELD OF THE INVENTION

The present invention relates generally to nucleotide sequences. More particularly, it relates to DNA sequences coding for at least a portion of the unique B cell activation antigen, B7. Expression vectors containing the nucleic acid sequences are introduced into host cells and direct the production of B7 proteins and peptides, which can be purified and included in pharmaceutical preparations that can be used to either enhance or suppress T cell mediated immune responses.

BACKGROUND OF THE INVENTION

All animals have a number of molecular and cellular components capable of interacting with and neutralizing various harmful foreign substances (antigens) in their environment. An animal's immune response to antigen involves both non-specific molecules and cells, as well as systems and mechanisms for the development of protective responses which possess memory and are extremely specific.

The primary cells of the immune system are the white blood cells, called lymphocytes, which are derived from cells in the bone marrow. One class of lymphocytes, the T lymphocytes, mature under the influence of the thymus and, upon stimulation by antigen, give rise to cellular immunity. T lymphocytes are also involved in the regulation of B lymphocytes, which, upon appropriate stimulation, mature into plasma cells that secrete antibody.

Mature T lymphocytes that emerge from the adult mammalian thymus migrate to peripheral lymphoid organs such as the spleen and lymph nodes. There, the naive T cells encounter antigens, usually in the form of processed peptides, bound to self molecules encoded by the major histocompatibility complex.

MHC class II molecules display peptides derived from proteins internalized through the endocytic pathway and are recognized predominantly by inducer T lymphocytes expressing the CD4 surface molecule. MHC class I molecules display peptides derived from proteins synthesized inside the antigen-presenting cell (for example, viral proteins) and are largely recognized by cytotoxic T lymphocytes expressing the CD8 surface molecule. Germain, *Nature*, 322:687 (1986).

The frequency of T cells specific for any given foreign antigen is initially small. If these cells are to play a central role in host defense, they must selectively increase in number. Thus, activation of the T lymphocyte upon recognition of foreign antigen leads to autocrine growth in which the stimulated naive cells proliferate in response to their own production of the polypeptide growth hormone interleukin-2 (IL-2) and the receptor for IL-2. Smith, *Annu. Rev. Immunol.*, 2:319 (1984); Greene et al, *Annu. Rev. Immunol.*, 4:69 (1986); Waldman, *Annu. Rev. Biochem.*, 58:875 (1989). In addition, the cells differentiate, acquiring the ability to produce other lymphokines, such as interleukin-4 (IL-4) and gamma interferon (IFN-γ) for $CD4^+$ cells. Swain et al, *J. Immunol.*, 141:3445 (1988); Salmon et al, *J. Immunol.*, 143:907 (1989); Gajewski et al, *Immunol. Rev.*, 111:79 (1989). These proteins serve as effector molecules for activating other cells in the immune system. IL-2 also plays a critical role in this recruitment function, as it can act in a paracrine fashion to help activated B lymphocytes and $CD8^+$ cytotoxic T lymphocytes expand in number.

The minimal requirement for an antigen-specific immune response is the effective binding of the processed peptide and the MHC molecule on an antigen-presenting cell by a clonally distributed T cell receptor for antigen. For most T cells, the T cell antigen receptor is a heterodimeric glycoprotein composed of two glycosylated protein chains, one of which is designated the alpha and the other, the beta, chain. Each of the two proteins chains is divided into variable (V) and constant (C) regions. The variable portions of the protein chains differ between T cell clones and are primarily responsible for the unique recognition specificity of a given T cell. These chains are non-covalently associated with another cell surface molecule, designated CD3, which is believed to be involved in signal transduction.

Although occupancy of the T cell receptor complex (TCR) by antigen in association with the major histocompatibility complex (MHC) is necessary for the initiation of T cell activation, several lines of evidence suggest that a second costimulatory signal is essential for the induction of proliferation and lymphokine secretion, particularly of interleukin-2. Schwartz, *Science*, 248:1349 (1990); Kawakami et al, *J. Immunol.*, 142:1818 (1989); Mueller et al, *J. Immunol.*, 142:2617 (1989); Williams et al, *J. Immunol.*, 145:85 (1990). In murine and human systems, one type of costimulatory signal is delivered by antigen presenting cells (APC) and requires cell to cell contact. Kawakami et al, *J. Immunol.*, 142:1818 (1989); Williams et al, *J. Immunol.*, 145:85 (1990). Cells which can deliver this costimulatory signal include activated, but not resting B lymphocytes (Ashwell et al, *J. Exp. Med.*, 159:881 (1984)); gamma-interferon (γ-INF) activated monocytes, and dendritic cells (Kawakami et al, *J. Immunol.*, 142:1818 (1989); Matis et al, *Proc. Natl. Acad. Sci. USA*, 80:6019 (1983)).

Several recent studies in human systems have provided compelling evidence that the B cell activation antigen B7 can provide one such costimulatory signal. Gimmi et al, "B7 provides a costimulatory signal which induces T cells to proliferate and secrete interleukin-2", *Proc. Natl. Acad. Sci. USA*, (in press); Linsley et al, *J. Exp. Med.*, 173:721 (March 1991); Koulova et al, *J. Exp. Med.*, 173:759 (March 1991).

The B7 activation antigen is a cell surface molecule that appears on the surface of a subpopulation of B lymphocytes within 24 hours after activation with EBV or anti-immunoglobulin. Freedman et al, *J. Immunol.*, 139:3260–3267 (1987). This antigen is present on a subpopulation of human splenic B lymphocytes that respond more rapidly to signals of B cell activation and proliferation. Specifically, B7+ B cells are not capable of independently responding to low molecular weight B cell growth factor or IL-2. However, after activation, the B7+ subpopulation of B cells more rapidly enters the S phase of the cell cycle in response to growth factors. The B7 antigen thus identifies a subpopulation of B cells that appear to be previously activated or primed in vivo and demonstrate accelerated growth to subsequent triggers.

Within the hematopoietic system, B7 is expressed on activated B cells and on monocytes that have been activated with gamma-interferon. In addition, B7 is present on some B lymphoblastoid and neoplastic cell lines, and on some tumor cells isolated from patients with certain types of B cell malignancies, particularly lymphomas.

B7 has recently been shown to be an adhesion ligand for another member of the immunoglobulin superfamily, the T cell surface protein CD28. Freeman et al, *J. Immunol.*, 143:2714 (1989); Aruffo et al, *Proc. Natl. Acad. Sci. USA*, 84:8573 (1987); Linsley et al, *Proc. Natl. Acad. Sci. USA*, 87:5031 (1990); Williams et al, *Ann. Rev. Immunol.*, 6:381 (1988). CD28 is constitutively expressed on 95% of human $CD4^+$ T cells, 50% of $CD8^+$ T cells, and on thymocytes which co-express CD4 and CD8. Turka et al, *J. Immunol.*, 144:1646 (1990); Yamada et al, *Eur. J. Immunol.*, 15:1164 (1985); Martin et al, *J. Immunol.*, 136:3282 (1986). Following suboptimal activation of T cells with anti-CD3 mAb; (Martin et al, *J. Immunol.*, 136:3282 (1986)); anti-CD2 mAb, or phorbol ester; (June et al, *J. Immunol.*, 143:153 (1989)) crosslinking of CD28 by anti-CD28 mAb results in enhanced T cell proliferation and greatly augments synthesis of multiple lymphokines. Thompson et al, *Proc. Natl. Acad. Sci. USA*, 86:1333 (1989). A method of immunotherapy involving stimulation of the T cell CD28 surface molecule to enhance T cell proliferation and increase lymphokine levels involving anti-CD28 monoclonal antibodies has been described. PCT International Publication Number WO 90/05541.

That B7 is likely to be an important regulator of T cell proliferation and lymphokine production is evidenced by its pattern of expression and functional activity described above. Further, human B7 transfected cells or recombinant B7-Ig fusion protein augment proliferation and induce interleukin-2 (IL-2), but not interleukin-4 (IL-4), synthesis in T cells which have been treated with phorbol ester or anti-CD3 mAb. Gimmi et al, "B7 provides a costimulatory signal which induces T cells to proliferate and secrete interleukin-2", *Proc. Natl. Acad. Sci. USA*, (in press); Linsley et al, *J. Exp. Med.*, 173:721 (1991); Koulova et al, *J. Exp. Med.*, 173:759 (1991).

Approaches to either upregulate or block the expression of B7 or the ligation of B7 to its natural ligand on T cells would provide a specific means of therapeutic intervention, to respectively enhance or suppress T cell-mediated immune responses in vivo. One approach involves the molecular cloning of B7, which would enable the recombinant preparation of B7 proteins. However, although the molecular structure of a number of other human B cell activation antigens has previously been determined, prior to the present invention, attempts to clone B7 were unsuccessful. Previously cloned B cell associated or restricted activation antigens include the nonlineage-restricted activation antigen 4F2 and transferrin receptor as well as the lymphoid-associated activation antigens, intracellular adhesion molecule-1, CD25, Blast-1 and CD23. The cDNA clones encoding various human B-cell associated antigens have been characterized through the use of expression techniques described by Aruffo and Seed (*Proc. Natl. Acad. Sci.*, 84:8573–8577 (1987); *Proc. Natl. Acad. Sci.*, 84:3365–3369 (1987)), including those encoding the B cell associated antigens CD19, CD20, CD22, CD27, CD39 and CDw40.

It is an object of the present invention to molecularly clone genes encoding the B7 activation antigen.

Another object of the invention is to provide nucleic acid molecules which code for the human and murine B7 B lymphocyte activation antigen.

Yet another object of the present invention is to provide a diagnostic method for quantitatively measuring activated B-cells in a biological sample.

A still further object of the present invention is to provide recombinantly produced B7 proteins.

These as well as other objects and advantages will be apparent from the following specification, drawing and claims.

SUMMARY OF THE INVENTION

These objects are achieved by the present invention, which provides isolated nucleic acid molecules encoding a B cell activation antigen, B7. In one embodiment, the molecule is a DNA molecule. In another embodiment of the invention, the DNA molecule comprises a nucleotide sequence that codes for at least a portion of the protein whose amino acid sequence shown in SEQ ID NO: 2. Further provided are nucleic acid molecules which encode proteins that are at least about 40% identical with the amino acid sequence set forth in SEQ ID NO: 2.

The DNA sequences obtained in accordance with the present invention can be integrated into various expression vectors, which in turn can direct the synthesis of the corresponding proteins or peptides in a variety of hosts, particularly eukaryotic cells, such as mammalian and insect cell culture. The expression vectors comprise a DNA sequence obtained in accordance with the present invention and a promoter operatively linked upstream of the DNA sequence. In general, depending upon the host cell used, the expression vectors will further contain regulatory elements, such as polyadenylation signals, RNA splice sites and enhancers.

An additional aspect of the present invention discloses host cells transformed to produce proteins or peptides encoded by the DNA molecules of the present invention.

Purified proteins and peptides which comprises at least a portion of the B cell activation antigen are also provided. These proteins and peptides comprise at least a portion of the mature form of the B7 activation antigen and preferably comprise a soluble form of the B7 protein. In one embodiment, the proteins and peptides are of human origin. In another embodiment, murine proteins and peptides are described.

The present invention also provides nucleic acid probes useful for assaying a biological sample for the presence of B cells expressing the B7 activation antigen.

BRIEF DESCRIPTION OF THE DRAWING

For a more complete understanding of the invention reference should now be made to the embodiments illustrated in greater detail in the accompanying drawing and described below by way of examples of the invention.

FIG. 4 provides a comparison of murine and human B7 amino acid sequences, which exhibit about 44% amino acid identity. The murine sequence (M) appears on the upper lines with the human sequence (H) directly below. Amino acid identities are indicated with a vertical bar (|). Potential N-linked glycosylation cites are marked with an *. The signal peptide, transmembrane and cytoplasmic domains are indicated. Ig-like domains are defined by the cysteines at positions 17 and 82 (Ig-V) and 128 and 182 (Ig-C).

DETAILED DESCRIPTION OF THE INVENTION

Figure 1:
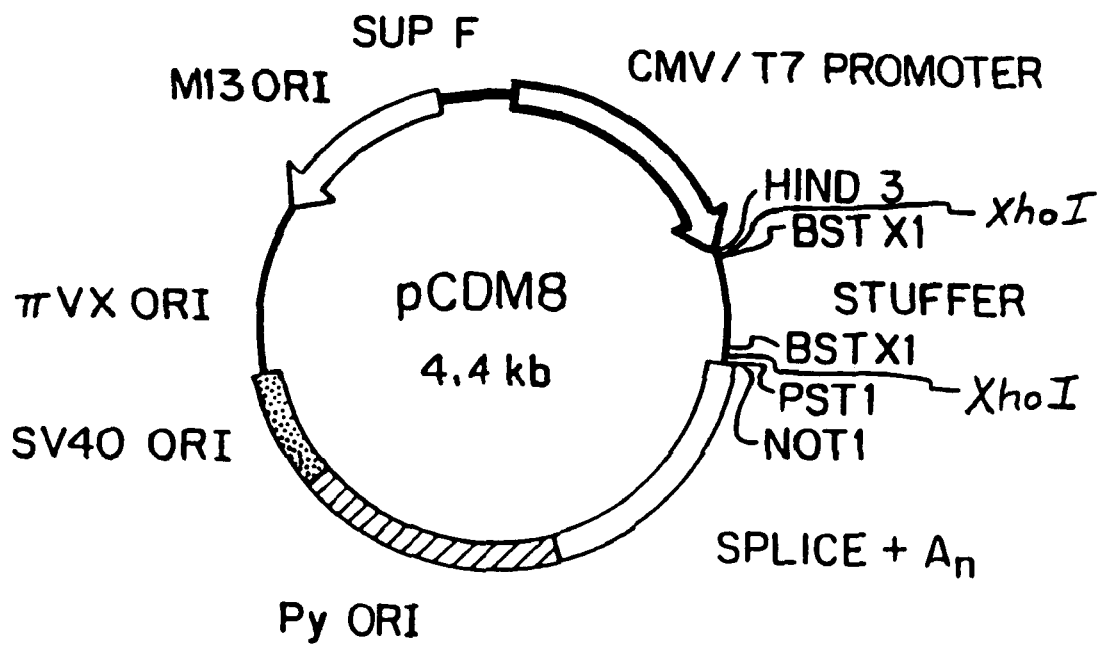
FIG. 1 illustrates the pCDM8 plasmid used in the cloning of human B7. The vector contains SV40, polyoma and πVX replication origins, a cytomegalovirus/T7 promoter and an M13 origin of replication. The pCDM8 vector was prepared for cloning of B7 by digestion with the restriction enzyme BstXI.

The human B7 activation antigen has previously been described by Freedman et al, *J. Immunol.*, 139:3260–3267 (1987). This activation antigen appears within 24 hours of in vitro stimulation of splenic B cells. The expression of the B7 antigen, which is detected on a minor subpopulation of B cells isolated from peripheral blood and lymphoid tissues, is strongly induced following stimulation with either anti-immunoglobulin or EBV. In contrast, B7 is not detected on resting or activated T cells or on resting monocytes. As illustrated in the examples herein, the human B7 antigen is expressed on a subset of B cell lines and B cell neoplasms, but is not generally detected on leukemias or lymphomas of T cell origin.

In accordance with the present invention, nucleic acid molecules encoding a B cell activation antigen, B7, are isolated. In one embodiment, the molecule is a DNA molecule and preferably comprises cDNA encoding at least a portion of the B7 activation antigen.

An exemplary, putative amino acid sequence based upon the experimentally determined nucleotide sequence for a human B7 activation antigen is provided in SEQ ID NO:2.

A total of 15 cDNA clones which code for the human B7 activation antigen have been isolated from a Burkitt's lymphoma cell line. These cDNA clones were identified by direct expression in COS monkey cells using the previously described B7 mAb in the screening process. Freedman et al, *J. Immunol.*, 139:3260 (1987).

The gene coding for the B7 activation antigen can be cloned from either a cDNA or a genomic library in accordance with protocols herein described. As an example, a cDNA nucleotide sequence for the B7 activation antigen can be obtained by isolating total mRNA from an appropriate cell line. Double stranded cDNAs are then prepared from the total mRNA. Subsequently, the cDNA's can be cloned by joining them to a suitable plasmid or bacteriophage vector using any one of a number of known techniques. B7 can also be cloned using established polymerase chain reaction techniques in accordance with the nucleic acid sequence information provided by the invention.

Cell Lines

Suitable cells for use in isolating human cDNA clones are those that can be shown to make mRNA coding for the B7 activation antigen and appropriately translating the B7 mRNA into the B7 protein. One source of mRNA is that obtained from normal human splenic B cells activated with anti-immunoglobulin or EBV or from subsets of neoplastic B cells. Expression of B7 transcripts in normal, stimulated cells is first detected about four hours after stimulation, with mRNA levels peaking at from 4–12 hours and declining slowly thereafter. Total cellular RNA can be obtained during these intervals and utilized in the construction of the cDNA library.

In addition, various subsets of neoplastic B cells are known to express B7 and can alternatively serve as a source of the mRNA for construction of the cDNA library. For example, tumor cells isolated from the majority of patients with non-Hodgkins lymphoma express B7 mRNA. B cells from nodular, poorly differentiated lymphoma (NPDL), diffuse large cell lymphoma (LCL) and Burkitt's lymphoma cell lines are suitable sources of human B7 mRNA. The Burkitt's lymphoma cell line Raji is a particularly preferred source of the B7 mRNA.

Isolation Of mRNA And Construction Of cDNA Library

Total cellular mRNA can be isolated by a variety of techniques, e.g. by using the guanidinium-thiocyanate extraction procedure of Chirgwin et al, *Biochemistry*, 18:5294–5299 (1979). If this method is utilized, Poly (A+) mRNA is prepared and purified for use in cDNA library construction using oligo (dT) cellulose selection. cDNA is then synthesized from the poly(A+) RNA using oligo(dT) priming and reverse transcriptase. Moloney MLV reverse transcriptase available from Gibco/BRL, Bethesda, Md., or AMV reverse transcriptase available from Seikagaku America, Inc., St. Petersburg, Fla., are preferably employed.

Following reverse transcription, the cDNA clone is converted to double stranded DNA using conventional techniques and incorporated into a suitable vector. The experiments herein employed *E. coli* DNA polymerase I and ribonuclease H in the conversion to double stranded DNA.

Cloning of the cDNA's can be accomplished using any of the conventional techniques for joining double stranded DNA with the vector. The use of synthetic adaptors is particularly preferred, since it alleviates the possibility of cleavage of the cDNA with restriction enzyme prior to cloning. Using this method, non-self complementary, kinased adaptors are added to the DNA prior to ligation with the vector. Virtually any adaptor can be employed. As set forth in more detail in the examples below, non-self complementary BstXI adaptors are preferably added to the cDNA for cloning, for ligation into a pCDM8 vector prepared for cloning by digestion with BstXI.

Eukaryotic cDNA's can only be expressed if they are correctly placed in a vector that supplies a strong eukaryotic promoter and appropriate origin of replication and other elements including enhancers, splice acceptors and/or donor sequences and polyadenylation signals. The cDNA's of the present invention are placed in suitable vectors containing a strong eukaryotic promoter, an origin of replication, an SV 40 origin of replication which allows growth in COS cells, and a cDNA insertion site. Suitable vectors include πH3, (Seed and Aruffo, *Proc. Natl. Acad. Sci.*, 84:3365–3369 (1987) πH3m (Aruffo and Seed, *Proc. Natl. Acad. Sci.*, 84:8573–8577 (1987)), pCDM7 and pCDM8 (Seed, *Nature*, 329:840–841 (1987), with the pCDM8 vector being particularly preferred. As illustrated in FIG. 1, pCDM8 contains both SV40 and polyoma replication origins, a cytomegalovirus/T7 RNA polymerase promoter, an M13 origin of replication. The vector also contains a πVX origin of replication, which permits replication in *E. coli*. pCDM8 is available commercially from In Vitro Gen, San Diego, Calif.

Transfection And Screening

The thus prepared cDNA library is then cloned by expression cloning techniques. The basic expression cloning technique has been described by Seed and Aruffo, *Proc. Natl. Acad. Sci. USA*, 84:3365–3369 (May 1987) and Aruffo and Seed, *Proc. Natl. Acad. Sci. USA*, 84:8573–8577 (December 1987), although important modifications to the technique are essential for the successful molecular cloning of B7.

Initially, plasmid DNA is introduced into a simian COS cell line (Gluzman, *Cell*, 23:175 (1981)) by known methods of transfection, and allowed to replicate and express the cDNA inserts. The cells are then treated with the monoclonal antibody to B7 and distributed on dishes coated with an anti-Ig M antibody. Under these conditions, cells expressing the B7 antigen and bound with B7 mAb adhere to the plates and the remaining cells are washed away. This general method of cell selection is known as "panning". Use of the anti-Ig M antibody in the panning procedure is critical to the success of the cloning. Employment of total anti-immunoglobulin antibodies as taught by the prior art, has been found by the inventors herein to be inadequate. This is presumably because the anti-Ig antibody contains insufficient anti-Ig M antibody to "pan" for cells having bound Ig M antibody.

After panning, episomal DNA is recovered from the panned cells and transformed into a competent bacterial host, preferably *Escherichia coli*. Plasmid DNA is subsequently reintroduced into COS cells and the cycle of expression and panning repeated at least two times. After the final cycle, plasmid DNA is prepared from individual colonies, transfected into COS cells and analyzed for expression of B7 by indirect immunofluorescence.

The B7 monoclonal antibody employed in the expression cloning was described by Freedman et al, *J. Immunol.*, 139:3260–3267 (1987), the pertinent portions of which are hereby incorporated by reference. Such a monoclonal antibody can be prepared by immunizing BALB/c mice for three consecutive weeks with about 5×10$^6$ normal splenic B cells activated for 3 days with total anti-immunoglobulin coupled to polyacrylamide beads. A booster can be administered 28 days after the final immunization. After somatic cell hybridization with a suitable myeloma cell line according to the technique of Kohler and Milstein, as modified (*Nature*, 56:495 (1977)), supernatants are removed and tested for the presence of hybridoma antibodies reactive with immunizing cells by indirect immunofluorescence. Producer clones are then screened on unstimulated splenic B cells and tumor cells, as described by Freedman et al, for clones strongly reactive with immunizing cells and tumor cells, but weakly reactive with unstimulated splenic B cells. The B7 monoclonal antibody is of the murine Ig M isotype, demonstrates reactivity with the Burkitt's lymphoma Raji cell line to a dilution of 1/25,000 and exhibits the pattern of reactivity as described by Freedman et al.

Sequencing

After cloning, plasmids are prepared from the clones strongly reactive with B7 mAb and sequenced. Any of the conventional sequencing techniques suitable for sequencing tracts of DNA about 1.4 kb or larger can be employed.

The sequence of a human B7 cDNA insert obtained from the Burkitt's lymphoma cell line Raji is comprised of 1491 nucleotides. The entire nucleotide sequence of the clone is provided in SEQ ID NO:1. A single long open reading frame begins at the first methionine codon at nucleotides 318–320 and extends to nucleotide 1181. The first methionine codon is embedded in a sequence, GCCATGG, consistent with the consensus translation initiation sequence, RCCATGG.

The protein predicted by the thus-obtained nucleotide sequence is set forth in SEQ ID NO:2. This polypeptide has the typical features of a type I membrane protein and has long hydrophobic regions near the amino terminus and close to the carboxyl terminus. The hydrophobic sequence at the amino-terminal end has the characteristics of a secretory signal peptide. Amino terminal sequencing of a soluble form of the human B7 protein purified from the culture media of B7 transfected CHO cells revealed that the signal peptide is cleaved after the thirty fourth amino acid, glycine. Mature human B7 thus begins with the amino acid sequence—valine—isoleucine—histidine—valine.

The predicted mature form of B7 contains 254 amino acids, $M_r$ 29,311 daltons, and consists of a 208 amino acid extracellular domain (amino acids 1–208) a twenty seven amino acid hydrophobic transmembrane region (amino acids 209–235) and a short cytoplasmic domain (amino acids 236–254). There are 8 potential N-linked glycosylation sites (Asn-X-Ser/Thr), all in the extracellular region. Glycosylation of the human B7 protein leads to an apparent molecular weight of 44–54 kd. The transmembrane region contains three cysteine residues that could be involved in either lipid derivitization or binding to other proteins. The cytoplasmic domain is composed of 19 amino acids and contains nine arginine residues. The cDNA clone did not contain a poly(A) tract or the most common polyadenylation signal, AATAAA; however, the alternate polyadenylation signal, ATTAAA, is present near the 3' end of the cDNA clone.

Cells transfected with the complete human B7 DNA sequence provide a costimulatory signal to human CD28$^+$ T lymphocytes that have received a primary activation signal, as evidenced by T cell secretion of IL 2 and enhanced T cell proliferation.

Cloning B7 From Other Mammalian Species

The present invention is not limited to human nucleic acid molecules and contemplates that B7 homologues from other mammalian species that express the B7 antigen can be cloned and sequenced using the techniques described herein. Isolation of cDNA clones from other species can also be accomplished using human cDNA inserts as hybridization probes as described in the examples.

The cloning and sequencing of the murine homologue of human B7 is illustrated in Example 8 herein and the nucleotide sequence set forth is SEQ ID NO:3. The predicted amino acid sequence for murine B7, illustrated in SEQ ID NO:4, has about 44% amino acid identity with human B7, with the greatest similarity being in the Ig-V and Ig-C like domains. See also FIG. 4. Cells transfected with murine B7 provide a costimulatory signal to both mouse and human T lymphocytes, which demonstrates the costimulatory activity of murine B7 and provides evidence that the T cell ligand attachment site(s) is conserved between the two species.

B7 nucleotide sequences from other species, such as the mouse, can be used to generate transgenic animals or "knock out" animals which, in turn, are useful in the development and screening of therapeutically useful reagents.

For example, murine cDNA or an appropriate sequence thereof can be used to clone for genomic B7 in accordance with established techniques and the genomic sequences used to generate transgenic animals that over-express B7. Methods for generating transgenic animals, particularly animals such as mice, have become conventional in the art and are described, for example, in U.S. Pat. Nos. 4,736,866 and 4,870,009. Typically, particular cells would be targeted for B7 transgene incorporation with tissue specific enhancers, which could lead to enhanced T cell proliferation and autoimmunity. Transgenic animals that include a copy of a B7 transgene introduced into the germ line of the animal at an embryonic stage can be used to examine the effect of increased B7 expression. Such animals can be used as tester animals for reagents thought to confer protection from, for example, autoimmune disease. In accordance with this facet of the invention, an animal is treated with the reagent and a reduced incidence of the disease, compared to untreated animals bearing the transgene would indicate a potential therapeutic intervention for the disease.

Alternatively, the non-human homologues of B7 can be used to construct a B7 "knock out" animal which has a defective B7 gene. An example of the construction of a B7 "knock out" mouse is provided in Example 10. Such animals can be characterized for their ability to accept grafts, reject tumors and defend against infectious diseases.

Expression Of The B7 Activation Antigen

Host cells containing a suitable expression vector which includes a nucleic acid molecule coding for a B7 activation antigen can be prepared and used to produce the proteins and polypeptides in accordance with methods known to those of ordinary skill in the art. The expression vectors of the present invention comprise a nucleic acid sequence coding for the B7 activation antigen, or any portion or fragment thereof. The vectors further comprise a promoter operatively linked upstream of the nucleic acid coding for B7. In general, depending upon the host cell used, the expression vectors will further contain regulatory elements, such as polyadenylation signals, RNA splice sites and enhancers.

Prokaryotes are very suitable hosts for expression of B7 proteins, assuming glycosylation is not desired. Preferred prokaryotes for carrying out the present invention are strains of the bacteria *Escherichia coli*, although Bacillus and other genera are also useful. Techniques for transforming these hosts and expressing foreign genes cloned in them are well known in the art. Vectors for expressing foreign genes in a bacterial host will usually contain a selectable marker, for example, a gene for antibiotic resistance, and will also contain a functional promoter.

Eukaryotic microorganisms, such as the yeast, *Saccharomyces cerevisiae*, may also be used as host cells.

Cell cultures derived from higher eukaryotic organisms are preferably used as the host cells. Particularly preferred are mammalian and insect cell cultures. Examples of useful mammalian host cell lines include HeLa cells, Chinese hamster ovary (CHO) cell lines, baby hamster kidney cell lines and COS cell lines. Insect cell lines, such as baculovirus infectable SF9 (*S. frugiperda*) are also useful host cells. Expression vectors for such cells ordinarily include, as necessary, an origin of replication, a promoter located upstream of the gene to be expressed, along with any required ribosome binding sites, RNA splice sites, polyadenylation sites and transcriptional terminator sequences. When used in mammalian cells, the expression vector's control functions are often provided by viral material. For example, commonly used promoters are derived from polyoma, Adenovirus 2, cytomegalovirus and most frequently, Simian Virus 40.

When utilizing eukaryotic systems for expressing B7, the host's glycosylation capability should be considered, since glycosylation may be important to the function and/or stability of B7.

Cloned gene sequences may be introduced into cultured cells using any of the known methods of transfection, including calcium-phosphate mediated transfection, electroporation and the like. A small fraction of the cells (about $1–10^5$) take up the DNA and integrate the DNA into their genomes. In order to identify these integrants, a gene that contains a selectable marker (i.e. resistance to antibiotics) is generally introduced into the host cells along with the gene of interest. Preferred selectable markers include those which confer resistance to drugs, such as neomycin, hygromycin and methotrexate. Selectable markers may be introduced on the same plasmid as the gene of interest or may be introduced on a separate plasmid.

Cells containing the gene of interest are identified by drug selection; cells that have incorporated the selectable marker gene will survive, while the other cells die. The surviving cells can then be screened for production of the B7 activation antigen by radiolabeling the proteins with a labeled amino acid and immunoprecipitating the B7 from the cell supernatant with anti-B7 monoclonal antibody.

Purification

The B7 proteins expressed in mammalian cells or otherwise can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22:233–577 (1971)). A preferred purification method involves a combination of immunoaffinity chromatography using anti-B7 monoclonal antibodies bound to Sepharose-CL4B and standard protein purification techniques. Once purified, partially or to homogeneity, the recombinantly produced B7 proteins of the invention can be utilized in pharmaceutical compositions as described in more detail below.

Modifications Of the B7 DNA Sequence

It will be appreciated by those skilled in the art that other nucleic acid molecules coding for the B7 activation antigen can be isolated by the above process. Different cell lines can be expected to yield DNA molecules having different sequences of bases. Additionally, variations may exist due to genetic polymorphisms or cell-mediated modifications of the genetic material. Furthermore, the DNA sequence of the B7 activation antigen can be modified by genetic techniques to produce proteins or peptides with altered amino acid sequences. Such sequences are considered within the scope of the present invention, where the expressed protein is capable of either enhancing or blocking activated T cell mediated immune responses and immune function.

A number of processes can be used to generate fragments, mutants and variants of the isolated DNA sequence. Small subregions or fragments of the B7 protein, for example 1–30 amino acids in length, can be prepared by standard, synthetic organic chemical means. The technique is also useful for preparation of anti-sense oligo nucleotides and primers for use in the generation of larger synthetic fragments of B7 DNA.

Larger subregions or fragments of the B7 gene can be expressed as protein by synthesizing the relevant piece of DNA using the polymerase chain reaction (PCR) (Sambrook, Fritsch and Maniatis, 2 *Molecular Cloning; A Laboratory Manual*, Cold Spring Harbor, N.Y., (1989)), and ligating the thus obtained DNA into an appropriate expression vector. Using PCR, specific sequences of the cloned double stranded DNA are generated, cloned into an expression vector, and then assayed for B7 activity. For example, to express a secreted (soluble) form of the human B7 polypeptide comprising amino acids 1–204, a PCR product is synthesized using the following two oligonucleotide primers and the B7 cDNA clone: (1) a sense primer consisting of a restriction enzyme site and 20 nucleotides corresponding to the translational initiation site and the first few amino acid codons of B7, and (2) an anti-sense primer consisting of 20 nucleotides corresponding to the last few amino acid codons of B7 ending at codon 204, (i.e., before the transmembrane region) followed by a stop codon and a restriction enzyme site. The PCR DNA product is then digested with the restriction endonuclease whose recognition sequence is in the PCR primers, gel purified, eluted, and ligated into an appropriate expression vector. The expression construct is introduced into a eukaryotic cell such as CHO, where the B7 polypeptide fragment is synthesized and secreted. The B7 polypeptide fragment can then readily be obtained from the culture media.

As used herein, the term "soluble B7" means an amino acid sequence corresponding to the extracellular domain of the B7 protein or any fragment thereof which does not include the cytoplasmic and/or transmembrane regions. Such polypeptides, when produced recombinantly in a host cell, will be secreted freely into the medium, rather than anchored in the host cell membrane.

Fragments of the B7 protein that would not include the normal B7 signal sequence, such as the region from amino acids 103–204 of the human protein, can be made as secreted, soluble proteins by performing a PCR using the following two oligonucleotide primers and the B7 cDNA clone: (1) a sense primer consisting of a restriction enzyme site and 20 nucleotides corresponding to amino acid codons 103–109 of B7, and (2) an anti-sense primer consisting of 20 nucleotides corresponding to the amino acid codons 198–204 of B7, followed by a stop codon and a restriction enzyme site. The PCR DNA product is digested with the restriction endonuclease whose recognition sequence is in the PCR primers, gel purified, eluted, and ligated in frame into an expression vector adjacent to a translational start site and signal sequence. The expression construct is then introduced into a eukaryotic cell such as CHO, where the B7 protein fragment is synthesized and secreted. The B7 protein fragment is again readily obtained from the culture media.

The foregoing fragments are provided for illustrative purposes only. It will be readily appreciated by those skilled in the art that a variety of fragments can be generated from the cDNA clone using the polymerase chain reaction. Particularly useful fragments can be made based upon knowledge of conserved amino acid sequences, for example, those regions of amino acid identity between mouse and human amino acid sequences illustrated in FIG. 4.

Alternatively, any one of the methods which have been developed for introducing mutations into cloned genes, including those for producing simple deletions or insertions, systematic deletions, insertions or substitutions of clusters of bases or substitutions of single bases, can be employed to generate variants of the B7 cDNA clone. Changes in the B7 sequence such as amino acid substitutions or deletions are preferably obtained by site-directed mutagenesis. Site directed mutagenesis systems are well known in the art. Protocols and reagents can be obtained commercially from Amersham International PLC, Amersham, U. K. As an example of the technique, amino acid 82 can be changed from a cysteine to a histidine, by making a mutagenesis oligonucleotide primer consisting of the codons for amino acids 79–81, a histidine codon (CAT) instead of the cysteine codon, and the codons for amino acids 83–85. This primer is then annealed to single-stranded antisense B7 phagemid DNA (made from the B7 cDNA clone in the pCDM8 vector) and the mutagenesis protocol followed. See, Oligonucleotide-directed in vitro mutagenesis system, Version 2, Amersham International PLC.

Fragments, mutants and variants of the B7 antigen that retain the ability to bind to their natural ligand(s) on T cells and either amplify or block activated T cell mediated immune responses, as evidenced for example by lymphokine production and/or T cell proliferation by T cells that have received a primary activation signal are considered within the scope of the invention. More specifically, B7 proteins and peptides that bind to T lymphocytes, for example $CD28^+$ cells, may be capable of delivering a costimulatory signal to the T lymphocytes, which, when transmitted in the presence of antigen and class II MHC, or other material capable of transmitting a primary signal to the T cell, results in activation of the T cell's lymphokine genes. Such B7 proteins can be considered to retain the essential characteristics of the B7 cell surface activation antigen. Alternatively, in accordance with the present invention it has been determined that some B7 proteins, and particularly soluble, monomeric forms of the B7 protein, retain the ability to bind to their natural ligand(s) on $CD28^+$ T cells but, perhaps because of insufficient cross-linking with the ligand, fail to deliver the secondary signal essential for enhanced lymphokine production and cell division. Such proteins, which provide a means to induce a state of anergy or tolerance in the cells, are also considered within the scope of the invention.

Screening the fragments, mutants or variants for those which retain characteristic B7 activity can be accomplished using one or more of several different assays. First, the fragments, mutants and variants can be screened for specific reactivity with an anti-B7 monoclonal antibody reactive with cell surface B7. Specifically, appropriate cells, such as CHO cells, can be transfected with the cloned variants and then analyzed for cell surface phenotype by indirect immunofluorescence and flow cytometric analysis. Cell surface expression of the transfected cells is evaluated using a monoclonal antibody ("mAb") specifically reactive with cell surface B7. Production of secreted forms of B7 is evaluated using anti-B7 mAb for immunoprecipitation.

Other, more preferred, assays take advantage of the functional characteristics of the B7 activation antigen. As previously set forth, the ability of T cells to synthesize lymphokines depends not only on occupancy or cross-linking of the T cell receptor for antigen ("the primary activation signal"), but also on the additional binding of a costimulatory signal, in this case, the B7 activation antigen. The binding of B7 to its natural ligand(s) on, for example, CD28 positive T cells, has the effect of transmitting a signal to the T cell that causes that cell to make much higher levels of lymphokines, particularly of interleukin-2 and gamma interferon, but also of lymphokines such as TNF $\alpha$, LT and GM-CSF, which in turn stimulates the proliferation of the T lymphocytes. Other assays for B7 function thus involve assaying for the synthesis of lymphokines, such as interleukin-2 (or gamma interferon) and/or assaying for T cell proliferation by $CD28^+$ T cells which have received a primary activation signal.

In vitro, T cells can be provided with the first signal by anti-T3 monoclonal antibody (e.g. anti-CD3) or phorbol ester or, more preferably, by antigen in association with class II MHC. B7 function is assayed by adding a source of B7 (e.g., cells expressing B7 or a fragment, mutant or variant thereof or a secreted form of B7) in association with Class II MHC and assaying the culture supernatant for interleukin-2 or gamma interferon. Any one of several conventional assays for interleukin-2 can be employed, such as the assay described in *Proc. Natl. Acad. Sci. USA*, 86:1333 (1989) the pertinent portions of which are hereby incorporated by reference. A kit for an assay for the production of interferon is available from Genzyme (Boston, Mass.). T cell proliferation can also be measured, as described in the Examples below. B7 proteins and peptides that retain the characteristics of cell surface B7 will cause increased production of lymphokines, such as IL-2 and may also result in enhanced T cell proliferation when compared to a negative control in which the secondary signal is lacking.

The same basic functional assays can also be used to screen for B7 proteins that are incapable of delivering the costimulatory signal, but in the case of such proteins, addition of the B7 protein will not result in a marked increase in proliferation or lymphokine secretion by the T cells. The ability of such proteins to block the normal B7 costimulatory signal and induce a state of anergy can be determined using subsequent attempts at stimulation of the T cells with antigen presenting cells that express cell surface B cell activation antigen B7 and present antigen. If the T cells are unresponsive to the subsequent activation attempts, as determined by IL-2 synthesis and T cell proliferation, a state of anergy has been induced. See, e.g., Schwartz, *Science*, 1348, 1352–1354, for a model assay system that can used as the basis for an assay in accordance with the present invention.

Utility

The nucleic acid molecules of the present invention are useful diagnostically, for tracking the progress of disease, by measuring the activation status of B cells in biological samples. In accordance with this diagnostic assay, the nucleic acid sequences are labeled with a detectable marker, e.g. a radioactive, fluorescent, or biotinylated marker or a $^{32}$P-labeled nucleotide and used in a conventional Northern hybridization procedure to probe mRNA molecules of total or poly(A+) RNAs from a biological sample.

In addition, the nucleic acid sequences and proteins can be used in the development of therapeutic reagents having the ability to either upregulate (amplify) or down regulate (suppress) T cell mediated immune responses. B7 proteins and peptides, including soluble, monomeric forms of the B7 activation, that fail to deliver a costimulatory signal to T cells that have received a primary activation signal, can be used to block the B7 ligand(s) on T cells and thereby provide a specific means by which to induce tolerance in an animal. In contrast to the monomeric form, multivalent forms of B7, such as cell surface B7, retain the ability to transmit the costimulatory signal to the T cells, resulting in an increased secretion of lymphokines when compared to activated T cells that have not received the secondary signal.

More specifically, now that the structure and function of B7 is known, it is possible to either upregulate or downregulate the function of B7 in one of a number of ways. Downregulating or preventing B7 function, i.e., preventing high level lymphokine synthesis by activated T cells, should be useful in autoimmune diseases such as rheumatoid arthritis and multiple sclerosis and also in tissue and organ transplantation. Blockage of T cell function leads to less tissue destruction. In tissue transplants, rejection of the transplant is initiated by its recognition as foreign, followed by an immune reaction that destroys the transplant. The administration of a soluble, monomeric form of B7 prior to transplantation can lead to the binding of monomeric B7 to its natural ligand(s) on T cells without transmitting the corresponding costimulatory signal and thus blocks the ligand on T cells. Blocking B7 function in this manner prevents T cell lymphokine synthesis and thus acts as an immunosuppressant.

In addition, in the acquired immune deficiency syndrome (AIDS), viral replication is stimulated by T cell activation. Blocking B7 function could lead to a lower level of viral replication and thereby ameliorate the course of AIDS. Surprisingly, HTLV-I infected T cells express B7. This expression may be important in the growth of HTLV-I infected T cells and the blockage of B7 function may slow the growth of HTLV-I induced leukemias.

One method of preventing B7 function is through the use of anti-sense oligonucleotides. For example, an oligonucleotide complementary to the area around the B7 translation initiation site, e.g., GTGGCCCATGGCTTCAGA, nucleotides 326–309, is synthesized. This anti-sense oligonucleotide can be added to cell media, typically at 200 μg/ml, or administered to a patient. The anti-sense oligonucleotide is taken up by cells and hybridizes to the B7 mRNA to prevent its translation. Thus, no B7 protein is made and the function B7 delivers is not performed.

The proteins or polypeptides produced from the nucleic acid molecules of the present invention may also be useful in the construction of therapeutic agents which block the B7 surface antigen. For example, as described, secreted forms of the B7 polypeptide can be constructed by standard genetic engineering techniques. By linking soluble B7 to a toxin such as ricin, an agent capable of preventing T cell activation would be made. Infusion of the immunotoxin, B7-ricin, into a patient would result in the death of T cells, particularly of activated T cells that express higher amounts of CD28. Soluble B7 in a monovalent form alone may be useful in blocking B7 function, as described above, in which case a carrier molecule may also be employed.

Upregulation of B7 function is also useful in therapy. For example, viral infections are cleared primarily by cytolytic T cells. In accordance with the present invention, it is believed that the interaction of B7 with its natural ligand(s) on T cells leads to an increase in the cytolytic activity of at least some T cells. The addition of soluble B7 in a multivalent form to stimulate T cell activity through the costimulation pathway would thus be therapeutically useful in cases where more rapid or thorough clearance of virus would be beneficial. These would include viral skin diseases such as Herpes simplex or shingles, in which cases the multi-valent soluble B7 is delivered topically to the skin. In addition, systemic viral diseases such as influenza, the common cold, and encephalitis might be alleviated by the administration of B7 proteins systemically.

The proteins and peptides of the present invention are administered in a biologically compatible form suitable for administration in vivo to either enhance or suppress T cell mediated immune response. By "biologically compatible form suitable for administration in vivo" is meant a form of the protein to be administered in which any toxic effects are outweighed by the therapeutic effects of the protein. Administration of the B7 proteins can be in any pharmacological form, which includes but is not limited to intravenous injection of a protein solution.

Alternatively, therapeutic intervention with the B7 proteins and peptides of the invention can involve removal of certain of a patients' activated T cells and costimulating the cells with B7 in vitro.

The present invention will be more clearly understood from the following specific examples. These examples are provided for illustrative purposes only and are not intended to limit the spirit or scope of the invention in any way.

EXAMPLE 1

This Example describes the molecular cloning and characterization of a human B7 B cell activation antigen.

Construction of cDNA Library

A cDNA library was constructed in the pCDM8 vector (Seed, *Nature*, 329:840 (1987)) using poly (A)+ RNA from the Burkitt lymphoma cell line Raji (Pulvertaft, *Lancet*, 1:238 (1964)) as described (Aruffo et al, *Proc. Natl. Acad. Sci. USA*, 84:3365 (1987)).

RNA was prepared by homogenizing Raji cells in a solution of 4M guanidine thiocyanate, 0.5% sarkosyl, 25 mM EDTA, pH 7.5, 0.13% Sigma anti-foam A, and 0.7% mercaptoethanol (15). RNA was purified from the homogenate by centrifugation for 24 hr at 32,000 rpm through a solution of 5.7M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol (16). RNA was ethanol precipitated twice. Poly (A)$^+$ RNA used in cDNA library construction was purified by two cycles of oligo (dT)-cellulose selection.

Complementary cDNA was synthesized from 5.5 $\mu$g of Raji cell poly(A)$^+$ RNA in a reaction containing 50 mM Tris, pH 8.3, 75 mM KCl, 3 mM MgCl$_2$, 10 mM dithiothreitol, 500 $\mu$M dATP, dCTP, dGTP, dTTP, 50 $\mu$g/ml oligo(dT)$_{12-18}$, 180 units/ml RNasin, and 10,000 units/ml Moloney-MLV reverse transcriptase in a total volume of 55 $\mu$l at 370° for 1 hr. Following reverse transcription, the cDNA was converted to double-stranded DNA by adjusting the solution to 25 mM Tris, pH 8.3, 100 mM KCl, 5 mM MgCl$_2$, 250 $\mu$M each dATP, dCTP, dGTP, dTTP, 5mM dithiothreitol, 250 units/ml DNA polymerase I, 8.5 units/ml ribonuclease H and incubating at 160 for 2 hr. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier. In addition, cDNA was synthesized from 4 $\mu$g of Raji cell poly(A)$^+$ RNA in a reaction containing 50 mM Tris, pH 8.8, 50 $\mu$g/ml oligo(dT)$_{12-18}$, 327 units/ml RNasin, and 952 units/ml AMV reverse transcriptase in a total volume of 100 $\mu$l at 42° for 0.67 hr. Following reverse transcription, the reverse transcriptase was inactivated by heating at 700 for 10 min. The cDNA was converted to double-stranded DNA by adding 320 $\mu$l H$_2$O and 80 $\mu$l of a solution of 0.1M Tris, pH 7.5, 25 mM MgCl$_2$, 0.5M KCl, 250 $\mu$g/ml bovine serum albumin, and 50 mM dithiothreitol, and adjusting the solution to 200 $\mu$M each dATP, dCTP, dGTP, dTTP, 50 units/ml DNA polymerase I, 8 units/ml ribonuclease H and incubating at 16° for 1 hr and 22° for 1 hr. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier.

The DNA from 4 $\mu$g of AMV reverse transcription and 2 $\mu$g of Moloney MLV reverse transcription was combined. Non-selfcomplementary BstXI adaptors were added to the DNA as follows: The double-stranded cDNA from 6 $\mu$g of poly(A)$^+$ RNA was incubated with 3.6 $\mu$g of a kinased oligonucleotide of the sequence CTTTAGAGCACA and 2.4 $\mu$g of a kinased oligonucleotide of the sequence CTCTAAAG in a solution containing 6 mM Tris, pH 7.5, 6 mM MgCl$_2$, 5 mM NaCl, 350 $\mu$g/ml bovine serum albumin, 7 mM mercaptoethanol, 0.1 mM ATP, 2 mM dithiothreitol, 1 mM spermidine, and 600 units T4 DNA ligase in a total volume of 0.45 ml at 150 for 16 hr. EDTA was added to 34 mM and the solution was extracted with an equal volume of 50% phenol, 49% chloroform, 1% isoamyl alcohol. DNA was precipitated with two volumes of ethanol in the presence of 2.5M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) was pooled and ethanol precipitated.

The pCDM8 vector was prepared for cDNA cloning by digestion with BstXI and purification on an agarose gel. Adaptored DNA from 6 $\mu$g of poly(A)$^+$ RNA was ligated to 2.25 $\mu$g of BstXI cut pCDM8 in a solution containing 6 mM Tris, pH 7.5, 6 mM MgCl$_2$, 5 mM NaCl, 350 $\mu$g/ml bovine serum albumin, 7 mM mercaptoethanol, 0.1 mM ATP, 2 mM dithiothreitol, 1 mM spermidine, and 600 units T4 DNA ligase in a total volume of 1.5 ml at 150° for 24 hr. The ligation reaction mixture was transformed into competent *E.coli* MC1061/P3 and a total of 4,290,000 independent cDNA clones were obtained.

Plasmid DNA was prepared from a 500 ml culture of the original transformation of the cDNA library. Plasmid DNA was purified by the alkaline lysis procedure followed by twice banding in CsCl equilibrium gradients (Maniatis et al, *Molecular Cloning: A Laboratory Manual*, Cold Spring Harbor, N.Y. (1987)).

Cloning Procedure

In the first round of screening, ten 100 mm dishes of 50% confluent COS cells were transfected with 1 $\mu$g/ml Raji library DNA using the DEAE-Dextran method (Seed et al, *Proc. Natl. Acad. Sci. USA*, 84:3365 (1987)). The cells were trypsinized and re-plated after 24 hr. After 47 hr, the cells were detached by incubation in PBS/0.5 mM EDTA, pH 7.4/0.02% Na azide at 37° C. for 30 min. The detached cells were treated with B7 mAb at a 1 to 500 dilution as described (18). Cells were washed and distributed into panning dishes coated with affinity-purified Goat anti-mouse IgM antibody (Southern Biotechnology Associates, Birmingham, Ala.) and allowed to attach at room temperature. After 3 hr, the plates were gently washed twice with PBS/0.5 mM EDTA, pH 7.4/0.02% Na azide, 5% FCS and once with 0.15M NaCl, 0.01 M Hepes, pH 7.4, 5% FCS. Episomal DNA was recovered from the panned cells and transformed into *E. coli* MC1061/P3. The plasmid DNA was re-introduced into COS cells via spheroplast fusion as described (Seed et al, *Proc. Natl. Acad. Sci. USA*, 84:3365 (1987)) and the cycle of expression and panning was repeated twice. After the third round, plasmid DNA was prepared from individual colonies and transfected into COS cells by the DEAE-Dextran method. Expression of B7 on transfected COS cells was analyzed by indirect immunofluorescence.

After the final round of selection, plasmid DNA was prepared from individual colonies. A total of 15 of 16 candidate clones contained a cDNA insert of 1.4–1.6 kb. Plasmid DNA from nine clones was transfected into COS cells. Five clones were strongly positive for B7 expression by indirect immunofluorescence using the anti-B7 mAb and flow cytometric analysis.

Sequencing

The B7 cDNA inserts were first subcloned into the SK plasmid (Stratagene, La Jolla, Calif.). DNA fragments were subcloned by first digesting with the XhoI restriction endonuclease and separating the DNA fragments by electrophoresis on an agarose gel. The appropriate fragment was cut out of the gel and eluted by the glass powder method ("Geneclean", Bio 101 Inc., La Jolla, Calif.). The SK plasmid vector was prepared by digestion with the appropriate restriction endonuclease followed by digestion with calf intestinal phosphatase to remove 5' phosphate residues from the DNA to prevent self-ligation. The phosphatase was then removed by phenol extraction. The dephosphorylated vector was purified by electrophoresis on an agarose gel. The vector was then cut out of the gel and eluted by the glass powder method.

Dephosphorylated vector was combined with the desired DNA fragment (with compatible ends) at a molar ratio of 1:1 or 1:2. The DNAs at approximately 40 µg/ml were ligated in 25 mM Tris, pH 7.8, 10 mM MgCl$_2$, 4 mM mercaptoethanol, and 0.4 mM ATP with T4 DNA ligase at a concentration of 1 unit/ml for sticky end ligations or 100 units/ml for blunt-end ligations. Ligations were carried out at 15° C. overnight. Ligated DNAs were transformed into competent E. coli and transformants selected by the appropriate antibiotic, 75 µg/ml Ampicillin.

Nested deletions were constructed using the Erase-a-base kit according to the manufacturer's instructions (Promega, Madison, Wis.). The cDNA inserts were then sequenced in their entirety on both strands using the dideoxy method of Sanger et al. (Sanger, et al, *Proc. Natl. Acad. Sci.*, 74:5463 (1977)). More specifically, sequencing was performed with Sequenase Version 2.0 (United States Biochemical Corp., Cleveland, Ohio), in accordance with the manufacturer's instruction. Sequenases are the enzymes of choice for determining large tracts of DNA, such as those obtained for the B7 clones, because of their high processivity, their high rate of polymerization and their wide tolerance for nucleotide analogs.

The sequence obtained is set forth in its entirety in SEQ ID NO:1.

Proof of identification of B7 clone

A. Immunofluorescence

COS cells were transfected with either vector DNA, CD2 DNA, or DNA from the largest B7 clone. Transfected COS cells were detached by incubation in PBS/0.5 mm EDTA/0.02% Na azide at 37° C. for 30 min. Viable cells were isolated by Ficoll-Hypaque density gradient centrifugation. Cells were analyzed for cell surface phenotype by indirect immunofluorescence and flow cytometric analysis. Cell surface expression of B7 and CD2 was evaluated using anti-B7 and anti-CD2 mAb (both murine IgM mAb), goat antimouse Ig FITC, and analyzed by indirect immunofluorescence. Only B7 transfected COS cells reacted with anti-B7 mAb whereas only CD2 transfected cells stained with anti-CD2 mAb. In contrast, vector-transfected, CD2-transfected, and B7-transfected COS cells demonstrated no significant staining with G/M-FITC alone. COS cells transfected with vector alone did not express either B7 or CD2.

The lack of binding of anti-CD2 to B7 transfected COS cells provided preliminary evidence that the B7 clone did not encode a nonspecific, IgM binding protein (Sanders et al, *J. Immunol.*, 139:188 (1987)). Five other IgM isotype mAb directed against lymphoid cell surface antigens were also examined for binding (anti-CD20 (pan-B), anti-CD14 (pan myeloid), anti-B5 (B activation), anti-Bac-1 (B activation), nd anti-BB-1 (B activation)). Anti-CD20, anti-CD14, anti-B5, and anti-Bac-1 were not reactive with B7-transfected COS cells; however, anti-BB-1 demonstrated strong staining. It has now been determined that the BB-1 and B7 activation antigens are one in the same.

B. Cell surface labeling and immunoprecipitation

The identity of the B7 antigen was further examined by immunoprecipitation.

COS cells were transfected with the B7 cDNA and cells were harvested after 65 hours. Viable Raji and B7 transfected COS cells were isolated by Ficoll-Hypaque density gradient centrifugation. Cell surface proteins were $^{125}$I-labeled by the lactoperoxidase conjugation technique (Boyd et al, *J. Immunol.*, 126:2461 (1981)) and cell lysates prepared as described (Tedeer et al, *J. Biol. Chem.*, 263:10009 (1988)). Cell lysates were precleared three times for 2 h each: once with 40 µl of a 50% (v/v) suspension of protein A-Sepharose CL-4B (Pharmacia Fine Chemicals, Piscataway, N.J.) per ml of lysate, once with 40 µl of a 50% (v/v) suspension of W6/32 (IgG2a mAb reactive with HLA-A, B, C Ag (Brodsky et al, *J. Immunol.*, 128:129 (1982)) coupled to cyanogen bromide activated Sepharose 4B (Pharmacia) and once with anti-CD20 (IgM isotype) rabbit anti-mouse IgM (25 µl of 1 mg/ml purified Ig) complex for 30 min. followed by the addition of protein A-Sepharose CL-4B. The precleared lysates were incubated for 30 min. at 4° C. with constant rotation with either: 1) anti-CD14 mAb (irrelevant mouse IgM mAb) rabbit anti-mouse IgM complex; 2) anti-BB-1 mAb rabbit anti-mouse IgM complex; or 3) anti-B7 rabbit anti-mouse IgM complex, followed by the addition of 20 µl of protein A-Sepharose for 3 h at 4° C. with constant rotation. Sepharose beads were washed with 1 ml of 100 mM Tris-HCl, pH 8.0, 1% (v/v) Triton X-100, 0.2% (w/v) sodium deoxycholate, 10 mM EDTA, 10 mM EGTA, 10 mM NaF, 1 mg/ml BSA containing 0.5 M NaCl followed by 1 ml of the same buffer containing 0.125 M NaCl, 0.2% (w/v) sodium deoxycholate, and 0.05% SDS. This wash cycle was repeated once. Precipitated proteins were eluted from the Sepharose beads by incubation in 50 µl of 125 mM Tris-HCl, pH 6.8, containing 2% (w/v) SDS, 5% 2-ME, 5% (v/v) glycerol, and 0.002% (w/v) bromphenol blue, in a boiling water bath for 4 min. Proteins were analyzed by 10% SDS-PAGE (Laemmli, Nature, 227:680 (1970)).

A SDS PAGE analysis showed a broad protein band of 44 to 54 kDa was specifically immunoprecipitated from B7 transfected COS cells by the anti-B7 mAb but not by anti-CD14. The anti-BB-1 mAb immunoprecipitated a polypeptide of identical molecular weight from B7 transfected COS cells. The B7 Ag on the Burkitt lymphoma cell line Raji was immunoprecipitated by anti-B7 as a 46-kDa band, whereas an isotype identical mAb demonstrated no immunoprecipitate.

EXAMPLE 2

DNA blot analysis of B7 gene

This experiment demonstrates that B7 is encoded by a single gene family.

DNA blot hybridizations using Nitroplus membranes (MSI, Inc., Westborough, Mass.) were performed as previously described (Maniatis et al, *Molecular Cloning: A laboratory Manual*, Cold Spring Harbor, N.Y. (1987); Feinberg et al, Anal. Biochem., 132:6 (1983)). Briefly, aliquots (5 µg) of human splenic DNA were digested with the restriction enzymes BamHI, EcoRI, PstI, HindIII, BglI, and KpnI, electrophoresed in 0.7% agarose, blotted and hybridized with the $^{32}$P-labeled B7 cDNA.

DNA blot analysis of the genomic organization of B7 revealed two or more DNA restriction fragments using the restriction endonucleases including BamHI, EcoRI, PstI, HindIII, BglI, and KpnI. These results were consistent with a one or two gene family. To distinguish between these possibilities, genomic DNA was digested with either EcoRI or HindIII, each of which produces two B7 specific restriction fragments, and the blot was probed with fragments isolated from the 5' or 3' ends of the B7 cDNA clone. The B7 5' probe hybridized with one of the EcoRI and HindIII fragments and the B7 3' probe hybridized with the other of the EcoRI and HindIII fragments. These results are consistent with B7 being encoded for by a single gene family encompassing a large genomic region.

EXAMPLE 3
Expression of Human B7 mRNA

In this example, the B7 cDNA clone was used to characterize the induction and lineage restriction of human B7.

A. Expression of B7 mRNA in in vitro-activated B cells.

Inasmuch as the B7 Ag appears on the surface of B cells after in vitro activation, it was of interest to determine whether its expression was transcriptionally regulated. Splenic cells were activated with anti-Ig. Total cellular RNA was harvested from the activated B cells at various times after activation, 0, ⅙, ½, 4, 8, 12, 24, 48, 72, and 96 hours, or from the Burkitt's lymphoma cell line, Raji. (Normal human spleen cells were obtained after securing appropriate Human Protection Committee validation and prepared as previously described. Boyd et al, *J. Immunol.*, 134:1516 (1985)). RNA was electrophoresed, blotted and probed with $^{32}$P-labeled B7 cDNA.

RNA blot analysis revealed no detectable B7 expression in unstimulated B cells. Expression was first detected at 4 h after activation. Four major RNA transcripts of 1.7, 2.9, 4.2, and 10 kb were observed with the 2.9-kb band being most intense. B7 mRNA levels peaked from 4 to 12 h and declined slowly thereafter with little mRNA detected after 48 h. In Raji, the cell line from which the B7 cDNA clone was derived, the 1.7-kb mRNA was the predominant form.

B. Expression of B7 mRNA in normal hematopoietic cells and cell lines.

To further characterize the induction and lineage restriction of B7, normal resting and activated hematopoietic cells were examined, as well as cell lines of T, B, and myeloid origins.

Whole resting spleen and splenic B cells did not express B7 mRNA. In contrast, splenic B cells activated with anti-Ig expressed the four major transcripts. Splenic B cells activated with TPA for 24 h did not express B7 mRNA. Granulocytes were negative whereas PHA-activated T cells and monocytes were very faintly positive. Cell lines of B cell origin including Raji, Daudi, and CESS were positive. The 1.7-kB mRNA predominated in the Burkitt's lymphoma lines, whereas the 1.7, 2.9, 4.2, and 10 kb species were all seen in CESS and activated B cells. The myeloma line U266 was negative whereas RPMI 8226 was very faintly positive. The T cell leukemia line Rex, the myeloid leukemic line KG-1 and the histiocytic cell line U937 were negative. However, the erythroleukemia line K562 was positive.

C. Expression of B7 mRNA on neoplastic B cells.

RNA blot analysis of B cell neoplasias revealed that B7 mRNA expression appeared to cluster in several histologically defined subgroups. Leukemias of B cell origin including non-T cell acute lymphocytic leukemia (ALL), prolymphocytic leukemia, hairy cell leukemia (HCL), and chronic lymphocytic leukemia (CLL) were generally negative although patients 5 (prolymphocytic leukemia), 6 (HCL), and 7 (HCL) weakly expressed the 10-kb transcript. In contrast, the majority of patients with non-Hodgkin's lymphoma expressed B7 mRNA. Eight of eight nodular poorly differentiated lymphomas (NPDL) expressed all four transcripts. Five of eight B cell diffuse large cell leukemia (LCL) were positive with most expressing all four transcripts. Two of three DPDL weakly expressed the 10-kb B7 transcript. Although most Burkitt's lymphoma cell lines were positive, two of two American Burkitt's lymphomas were negative. Only one of five myelomas were positive and the one Waldenstrom's was negative. The pattern of B7 expression found by Northern blot analysis is somewhat different than that reported for indirect immunofluorescence with the B7 mAb (Freedman et al, *J. Immunol.*, 139:3260 (1987)). In particular, by indirect immunofluorescence, most CLL but few NPDL were found to express B7 (Freedman et al, *J. Immunol.*, 139:3260 (1987)). The B7 mAb is an IgM and the low level of cell surface expression observed in CLL may be due to binding by the 60-kD IgM-binding protein expressed by many CLL (Sanders et al, *J. Immunol.*, 139:188 (1987)). In NPDL, the level of expression of B7 mRNA differed widely and the lower levels of B7 mRNA expression may correspond to levels of protein below the detection limit of indirect immunofluorescence.

It was of interest to note that the majority of circulating B cell leukemias did not express B7 mRNA whereas most solid lymphoid tumors were B7$^+$. Of the non-Hodgkin's lymphomas that did not express B7 mRNA, the two diffuse LCL were circulating and one of the two Burkitt's lymphomas was in an ascites form in vivo. To further explore this specificity of B7 expression, B7 mRNA expression was examined in a previously untreated patient where tumor replaced lymph node and simultaneous circulating tumor cells were present. NPDL cells isolated from the peripheral blood (more than 90% tumor cells) of this patient demonstrated only a very faint amount of 10-kb B7 transcript, whereas his lymph node NPDL cells (more than 90% tumor cells) were strongly positive, expressing all four transcripts. Southern blot analysis of IgH rearrangements showed the presence of equal amounts of clonally rearranged tumor in peripheral blood and lymph node samples from this patient.

EXAMPLE 4
Protein Homologies of B7

A search (Pearson et al, *Proc. Natl. Acad. Sci. USA*, 85:244 (1988)) of the GENBANK (release 59) and NBRF (release 19) databases revealed homology of B7 to members of the Ig superfamily. The homologies to members of the Ig superfamily are due to the presence of two contiguous Ig-like domains in the extracellular region between residues 1–104 and 105–202. Ig-like domains share a common three-dimensional structure composed of two β-sheets linked by an intradomain disulfide bond. Ig domains have been divided into V, C1, and C2 sets based on conserved amino acid patterns and the number of antiparallel β-strands composing the domain (Williams et al, *Annu. Rev. Immunol.*, 6:381 (1988)).

In B7, the cysteine residues at 16 and 82 define a potential disulfide-linked Ig domain with an intercysteine distance of 66 amino acids, typical of V set sequences. The predicted secondary structure (Chou et al, *Annu. Rev. Biochem.*, 47:251 (1978)) of the B7 Ig domain 1 is consistent with the 9 antiparallel β-strands of a V domain including the additional C' and C" strands. The conserved Asp-X-Gly adjacent to β-strand F and the Arg at the base of β-strand D are characteristic of V set sequences with the Asp and Arg residues forming a salt bridge within the Ig domain. The second Ig domain in B7 is defined by the cysteine residues at 128 and 182. The intercysteine distance of 54 residues is typical of C set sequences and the predicted secondary structure (Chou et al, *Annu. Rev. Biochem.*, 47:251 (1978)) is consistent with the seven antiparallel β strands of C set sequences. This domain is more closely related to the C1 than the C2 set and amino acids conserved in the C1 set and present in domain 2 are boxed in FIG. 4b.

The B7 Ig domains were compared with other members of the Ig superfamily using the ALIGN program (Dayhoff et al, *Methods Enzymol.*, 91:524 (1983)). ALIGN scores greater than 3.0 are considered statistically significant. The closest relationship between B7 Ig domain 1 and members of the Ig superfamily is with murine TCR gamma-chain variable region (ALIGN score of 7.65, 36.2% identity over 94 amino acids. The closest relationship between B7 Ig domain 2 and members of the Ig superfamily is with the human IgA-CH1 domain (ALIGN score of 6.85, 36.5% identity over 63 amino acids. The murine B29 protein is a member of the Ig superfamily whose expression is B cell restricted (Hermanson et al, *Proc. Natl. Acad. Sci. USA*, 85:6890 (1988)). The single Ig domain of B29 is distantly related to the B7 Ig domains (ALIGN scores of 2.68 and 4.70 for B7 Ig domains 1 and 2, respectively). In addition, residues 54–183 of B7 were moderately similar to the second and third Ig domains (residues 161–289) of the murine neural cell adhesion molecule (Cunningham et al, *Science*, 236:799 (1987)) (ALIGN score of 10.96, 23.8% identity over 126 amino acids).

EXAMPLE 5

This Example describes the preparation and purification of a soluble (secreted) form of human B7.

Production of Soluble B7

In order to produce large amounts of soluble B7, a plasmid encoding a secreted form of B7 was introduced into a eukaryotic cell and a stable cell line expressing B7 was selected.

In more detail, a DNA fragment encoding a secreted form of B7 was constructed by polymerase chain reaction (PCR) as follows: The original B7 cDNA clone in pCDM8 was excised by digestion with the restriction endonuclease XhoI. The digested DNA was phenol extracted and ethanol precipitated. A PCR reaction was performed using 50 nanograms of this DNA in 10 mM Tris, pH 8.3, 50 mM KCl, 1.5 mM $MgCl_2$, 0.001% gelatin, 200 micromolar dATP, dCTP, dGTP, dTTP, 25 unit/ml Taq DNA polymerase, and 25 picomoles each of a sense and an antisense oligonucleotide primer in a final volume of 100 microliters. The sense oligonucleotide primer had the sequence GCGAGAAT-TCGGATCCGCCACCATGGGCCACACACGG and contains recognition sites for the restriction enzymes EcoRI (GAATTC) and BamHI (GGATCC), a strong translation initiation site (CCACCATGG) and is identical to the B7 cDNA from nucleotides 316–332. The antisense primer has the sequence CGCTGAATTCGGATCCTAATGCTCT-TGCTTGGTT and contains recognition sites for the restriction enzymes EcoRI (GAATTC) and BamHI (GGATCC), a stop codon (sense TAG, antisense of CTA), and is identical, in an antisense orientation, to nucleotides 1016–1031.

The reaction mixture was covered with mineral oil. The PCR reaction was performed on a Techne programmable thermal cycler with 10 cycles of 94°, 1 m, 42°, 1 m, 72°, 1 m and a final cycle of 72°, 10 m. The resulting DNA product extended from B7 nucleotides 316–1031, followed by a stop codon, and was flanked by restriction enzyme sites. In the cell, this DNA encodes a secreted form of the B7 protein from amino acids methionine −34 to histidine 204.

Following completion, the reaction was phenol-chloroform extracted, made 2.5M in ammonium acetate, and ethanol precipitated. The DNA was redissolved and digested with 40 units of BamHI. The DNA fragment was electrophoresed in an agarose gel, eluted, and ligated into BamHI digested, calf intestinal phosphatase treated, pLEN. pLEN is an expression vector that contains a BamHI cloning site between the strong metallathione II promoter and the 3' untranslated region and polyadenylation site of human growth hormone, signals necessary for expression in mammalian cells. In addition, the vector contains the SV40 enhancer, pUC8 origin of DNA replication, and ampicillin resistance gene. A second plasmid, pSV2-Neo, expressing a selectable marker, neomycin resistance, was introduced into the cell at the same time as the secB7-pLEN plasmid in order to provide a selectable marker for DNA integration (Neo). The plasmids were first linearized by cutting with a restriction enzyme, PvuI, that cuts in a non-essential region of the plasmids. The linearized plasmids were introduced into CHO-K1 cells by electroporation. Cells were resuspended in media without fetal calf serum and 50 micrograms of linearized secB7-pLEN and 5 micrograms of linearized pSV2-Neo were added to the solution. The membranes of the cells were momentarily opened by an electric current of 250 volts, 1600 mF (Bio-Rad Corp., Richmond, Calif.) allowing the plasmids to enter the cell. The plasmid DNAs were stably incorporated into the chromosome of the CHO-K1 cells at some low rate, about 1 in 100,000. It has been shown that while this incorporation is rare, when it does take place, a large amount of DNA is incorporated. Thus, if the pSV2-Neo plasmid is incorporated, the secB7-pLEN is also likely to be incorporated. The cells incorporating the DNA were selected for by adding 400 micrograms/ml of G418, a form of neomycin, to the media. Cells that incorporated the pSV2-Neo survive while other cells died.

Surviving cells were analyzed for the secretion of B7 by radiolabeling the proteins with $^{35}$S-methionine and immunoprecipitating B7 from the cell supernatant with anti-B7 mAb. Cells expressing secreted B7 were cloned and grown up in large numbers. Secreted B7 was purified from the cell supernatant as follows. The supernatant was first applied to a Lentil Lectin column, and the B7 protein was eluted with 5% methyl-α-D-mannopyranoside in PBS. The eluted material was dialyzed against 50 mM Tris pH 8.3, 10 mM NaCl, and applied to a Q-sepharose (Pharmacia) column equilibrated in 50 mM Tris pH 8.3, 50 mM NaCl.

The protein was next eluted with a linear salt gradient from 0.05–0.5M NaCl. The B7 protein eluted at approximately 0.25M NaCl as assayed by polyacrylamide gel electrophoresis. B7 containing samples were pooled and concentrated via an Amicon ultrafiltration stirred cell using a 10 Kd MW cut-off membrane, then passed over an S-200 gel filtration column equilibrated with 50 mM Tris pH 8.3, 250 mM NaCl. Relevant B7 fractions were pooled.

The thus-prepared soluble B7 was then screened for B7 activity in accordance with the following assay.

$1 \times 10^5$ normal T cells isolated from peripheral blood were cultured in 96 well flat bottom plates with either media alone or phorbol myristic acetate (2.5 ng/ml, final conc.), with either anti-CD28 monoclonal antibody 1 μg/ml (final conc.) (positive control), ionomycin (100 ng/ml, final conc.) positive control, or the soluble B7 protein (used at a 1:4 dilution, final concentration), or media alone. This assay has been published in *Proc. Natl. Acad. Sci. USA*, 86:1333, (1989) the pertinent portions of which are incorporated by reference. The T cells were cultured at 37° for 24 h, then the supernatants were harvested and assayed for IL-2 activity in a bioassay. The IL-2 assay involved using an ELISA IL-2 assay (described in Example 7), standard curves were calculated and the concentration of IL-2 produced by the test samples determined. The results of the experimentation demonstrated that, while the anti-CD28 monoclonal antibody caused a marked enhancement in the secretion of IL-2 by normal, suboptimally stimulated T cells, the soluble form of B7 failed to show any significant increase in interleukin-2 production.

Without wishing to be held to any theory or mechanism of the invention, the inventors herein have preliminarily determined that the inability of this soluble B7 to enhance IL-2 secretion is the result of its inability, in monomeric form, to cross-link its natural ligand on T cells, an event that is required for signal transduction (Linsley et al, *J. Exp. Med.*, 173:759 (1991)).

EXAMPLE 6

This Example describes the amino terminal sequencing of a soluble form of human B7.

N-terminal Amino Acid Sequence of Human B7

A secreted, soluble form of hB7 was synthesized in CHO cells and purified from CHO cell supernatants as described in Example 5. Purified B7 was run on a 9% polyacrylamide gel and electroblotted onto an Immobilon-P polyvinylidene diflouride (PVDF) transfer membrane (Millipore, Bedford, Mass.) in 10 mM CAPS (3-(cyclohexylamino)-1-propanesulforic acid), pH 11.0 and 10% methanol. The membrane was stained with Coomasie Blue to identify the B7 protein band.

The B7 protein band was excised and the N-terminal amino acid sequence was determined using an Applied Biosystems 477A protein sequencing system. The N-terminal amino acid sequence was determined to be Val, Ile, His, Val, Thr, Lys, Glu, Val, Lys, Glu.

EXAMPLE 7

This example demonstrates that multivalent B7, in the form of B7 transfected CHO cells, can induce suboptimally activated CD 28+ T lymphocytes to proliferate and cause the secretion of high levels of interleukin 2.

Materials And Methods

A. Cells.

Human peripheral blood mononuclear cells were isolated from buffy coats obtained by leukopheresis of healthy donors. After density gradient centrifugation, the cells were further purified by depletion of adherent cells on plastic. Residual B cells and monocytes were depleted by passage through nylon wool. The CD28$^+$ subset of T cells was enriched by separation from the reciprocal subset of CD11$^+$ T cells (June et al, *Mol. Cell. Biol.*, 7:4472–4481 (1987); Damle et al, *J. Immunol.*, 131:2296–2299 (1983); Yamada et al, *Eur. J. Immunol.*, 15:1164–1172 (1985), residual B cells, and monocytes by two treatments with complement lysis utilizing anti-3B8 (CD56), anti-Mol (CD11B), anti-Mo2 (CD14) and anti-B1 (CD20) mabs. The efficiency of the purification process was analyzed in each case by indirect cell immunofluorescence and flow cytometry (Coulter EPICS flow cytometer) using T3 (CD3) and 4B10 (CD28) mAbs and fluorescein isothiocyanate-labeled goat anti-mouse immunoglobulin (Tago, Burlingame, Calif.). The final T cell preparation was >90% CD3$^+$ and >88% CD28$^+$ in each case when compared with staining with an isotype identical unreactive control antibody. Examination of smears stained for nonspecific esterase (α naphthyl acetate esterase; SIGMA, St. Louis, Mo.) confirmed that the cell population contained about 1% monocytes.

B. mAbs.

4B10 (IgG1) is an anti-CD28 mAb that immunoprecipitates a 44-kDa disulfide-bonded dimer and enhances proliferation and lymphokine synthesis of suboptimally activated T cells. Indirect immunofluorescence of CD28-transfected COS cells revealed about 5% positive cells with similar intensities of staining using 4B10 or the anti-CD28 mAbs YTH 913.12 and 9.3 (Hara et al, *J. Exp. Med.*, 161:1513–1524 (1985)). YTH 913.12 was kindly provided by H. Waldmann. Optimal stimulation with anti-CD28 mAb was obtained at a concentration of 1 µg/ml and this dose was used throughout the experiments. Anti-CD3mAb OKT3 (IgG2a) was obtained from the American Type Culture Collection and was adhered to plastic plates at a concentration of 1 µg/ml. This concentration was found to produce optimal stimulation in association with a second signal of T-cell activation. 4B10 and OKT3 were purified using a protein A-agarose column (Bio-Rad) as described (Van Wauwe et al, *J. Immunol.*, 124:2708 (1980)). The anti-B7 mAb 133 (IgM) was characterized in our laboratory (Freeman et al, *J. Immunol.*, 143:2714–2722 (1989); Freedman et al, *J. Immunol.*, 139:3260–3267 (1987)), and was used as ascites at a final dilution of 1:100.

C. B7 Transfection.

The B7 cDNA clone in the pCDM8 vector obtained as in Example 1 was digested with restriction endonucleases DraI and BglII, and the fragment comprising nucleotides 86–1213, containing the coding region of B7, was isolated. The DraI-BglII fragment was ligated into BamHI-digested, phosphatase-treated pLEN by a combination of sticky-end ligation, Klenow polymerase fill-in, and blunt-end ligation. pLEN is a eukaryotic expression vector containing the human metallothionein IIA promoter, the simian virus 40 enhancer, and the human growth hormone 3' untranslated region and polyadenylation site (Friedman et al, *Bio/Technology*, 7:359–362 (1989). pLEN was kindly provided by Metabolic Biosystem (Mountain View, Calif.). Fifty micrograms of PvuI-linearized B7-pLEN construct was cotransfected with 5 µg of PvuI-linearized SV2-Neo-Sp65 into CHO-KI Chinese hamster ovary cells by electroporation using the BRL electroporator at settings of 250 V and 1600 mF. Transfectants were selected by growth in medium containing the neomycin analogue G418 sulfate (400 µg/ml) and were cloned. Clones expressing cell surface B7, as assayed by indirect immunofluorescence with anti-B7 mAb, were recloned. These cells are referred to as CHO-B7 cells. Mock-transfected CHO-K1 (CHO-mock) cells were made by transfection of PvuI-linearized SV2-Neo-Sp65 alone.

D. Cell Fixation.

CHO cells were detached from tissue culture plates by incubation in Dulbecco's phosphate-buffered saline (PBS) with 0.5 mM EDTA for 30 min. Cells were washed once in PBS and resuspended in PBS at 10$^7$ per ml. An equal volume of freshly prepared 0.8% paraformaldehyde in PBS was added and the cells were gently mixed for 5 min. at room temperature. An equal volume of 0.2 M lysine in PBS was added to block unreacted paraformaldehyde and the cells were pelleted by centrifugation. The cells were washed once in PBS, once in RPMI 1640 (Whittaker Bioproducts) containing 10% heat-inactivated fetal bovine serum (Sigma), resuspended in the same medium, and incubated for 1 hr. in a humidified 37° C. incubator. Cells were pelleted, washed in RPMI 1640 containing 10% heat-inactivated human AB serum (North American Biologicals, Miami), 2 mM glutamine, 1 mM sodium pyruvate, penicillin (100 units/ml), streptomycin sulfate (100 µg/ml), and gentamicin sulfate (5 µg/ml) (Gibco). Cells were resuspended in this medium containing heat-inactivated human AB serum and 2×10$^4$ fixed cells were added to the appropriate wells in a 96-well flat-bottomed microtiter plate (Nunclon; Nunc).

E. Proliferation Assay.

CD28+ T lymphocytes were incubated in RPMI 1640 containing 10% heat-inactivated human AB serum, 2 mM glutamine, 1 mM sodium pyruvate, penicillin (100 units/ml), streptomycin sulfate (100 μg/ml) and gentamicin sulfate (5 μg/ml). Cells were cultured at a concentration of 5–10$^4$ cells per 200 μl of medium in triplicate samples in a 96-well flat-bottomed microtiter plate at 37° C. for 3 days in 5% $CO_2$. Cells were cultured in medium and with the appropriate stimuli added. Cells were stimulated with PMA (Calbiochem) at 1 ng/ml and ionomycin (Sigma) at 100 ng/ml (Manger et al, *J. Immunol.*, 139:2755–2760 (1987); Wiskocil et al, *J. Immunol.*, 134:1599–1603 (1985); June et al, *J. Immunol.*, 143:153–161 (1989)). The anti-CD3 mAb was added at 1 μg/ml to the 96-well flat-bottomed microtiter plates and incubated at room temperature for 1 hr; the plates were then washed twice with PBS before addition of the cells (Weiss et al, *J Immunol.*, 137:819–825 (1986); Manger et al, *J. Immunol.*, 139:2755–2760 (1987); Matsuyama et al, *J. Exp. Med.*, 170:1133–1148 (1989); Geppert et al, *J. Immunol.*, 138:1660–1666 (1987)). The anti-CD28 mAb 4B10 was added at 1 μg/ml. The fixed CHO-B7 and CHO-mock transfectants were added at 2–104 cells per well. Preliminary experiments showed that maximal stimulation plateaued with the addition of 2–104 CHO-B7 cells. The specificity of the stimulation with CHO-B7 cells was assayed by the addition of anti-B7 mAb to the cultures at a final ascites dilution of 1:100. Over the wide range of concentrations (1:50 to 1:2000) assayed, this dose was found to produce complete blocking of CHO-B7 stimulation.

F. Thymidine Incorporation Assay.

Thymidine incorporation was used as an index of mitogenic activity. During the last 8 hrs. of the 72-hour culture, the cells were incubated with 1 μCi of (37 kBq) of [methyl-$^3$H]thymidine (ICN Flow, Costa Mesa, Calif.). The cells were harvested onto filters and the radioactivity on the dried filters was measured in a Packard Tri-Carb scintillation counter.

G. Lymphokine Assay.

Culture supernatants were collected 24 hrs. after the initiation of the culture and IL-2 and IL-4 concentrations were assayed in duplicate using an ELISA kit according to the manufacturer's instructions (Quantikine; R 7 D Systems, Minneapolis, Minn.).

Results

A. B7-Transfected CHO Cells Stimulate Proliferation of Suboptimally Activated CD28+ T Cells.

Crosslinking of CD28 on T cells by anti-CD28 mAb has been shown to stimulate T-cell proliferation and lymphokine synthesis (June et al, *J. Immunol.*, 143:153–161 (1989)). Since B7 is a natural adhesion ligand for CD28, we attempted to determine whether binding of cell surface B7 to CD28 positive T cells would deliver a costimulatory signal to T cells. To this end, a CHO cell line expressing high levels of B7 (CHO-B7) was constructed by stable transfection of the B7 gene under the control of the strong metallothionein promoter. The CHO-B7 cells were fixed with paraformaldehyde and used to stimulate CD28+ cells that had been suboptimally stimulated with phorbol myristic acetate (PMA) or anti-CD3.

As seen in Table 1 below, PMA, 1 ng/ml, induced a 3- to 8-fold increase in T-cell proliferation over the medium-only controls. Addition of paraformaldehyde-fixed CHO-B7 cells to PMA-activated CD28+ T cells stimulated proliferation 17- to 40-fold. Addition of anti-CD28 mAb also enhanced CD28+ T-cell proliferation 26- to 58-fold compared with cells cultured with PMA alone. The stimulation by CHO-B7 was ≈28% less than that observed with anti-CD28 mAb in all experiments performed. CHO-mock cells did not induce proliferation over background, providing evidence that B7 was specifically inducing the proliferation signal. Neither anti-CD28 mAb nor CHO-B7 cells were able to induce proliferation of untreated CD28+ cells. Cultures of the paraformaldehyde-fixed transfected CHO cells alone showed no proliferation over medium controls. Table 1 depicts T cells from 3 representative, normal donors and similar results have been consistently observed in seven independent experiments.

TABLE 1

Effect of phorbol ester, anti-CD28, and CHO-B7 cells on proliferation of CD28+ T Cells

| CD28+ cell treatment | [$^3$H] Thymidine incorporation, cpm (mean ± SEM) | | |
|---|---|---|---|
| | Donor 1 | Donor 2 | Donor 3 |
| Medium control | 156 ± 65 | 130 ± 11 | 151 ± 29 |
| PMA | 1,404 ± 386 | 1,032 ± 176 | 537 ± 73 |
| Anti-CD28 | 88 ± 18 | 109 ± 6 | 188 ± 6 |
| CHO-B7 | 104 ± 6 | 102 ± 9 | 143 ± 37 |
| PMA + CHO-B7 | 57,030 ± 1,017 | 34,560 ± 4,961 | 9,440 ± 1,103 |
| PMA + anti-CD28 | 82,263 ± 1,137 | 45,023 ± 2,684 | 14,215 ± 1,682 |
| PMA + CHO-mock | 1,010 ± 228 | 728 ± 163 | 369 ± 36 |
| PMA + CHO-B7 + anti-B7 | 1,041 ± 434 | 737 ± 78 | 559 ± 52 |
| PMA + CD28 + anti-B7 | 76,697 ± 1,241 | 48,776 ± 712 | 15,290 ± 2,011 |

To confirm that the increased proliferation observed in the PMA-treated CD28+ T cells was specifically mediated through ligation to B7, anti-B7 mAb was added to the culture system to block this binding. The addition of anti-B7 mAb totally abrogated the proliferative response induced by the CHO-B7 cells (Table 1). In contrast, anti-B7 mAb had no effect on the stimulation of proliferation induced by anti-CD28 mAb. These results further confirm that B7 provided the costimulatory signal.

To determine whether binding of B7 to CD28 could augment proliferation of T cells that had received a first signal of T-cell activation through the TCR, CD28+ T cells were first submitogenically stimulated with anti-CD3 mAb fixed to plastic (Weiss et al, *J. Immunol.*, 137:819–825 (1986); Manger et al, *J. Immunol.*, 139:2755–2760 (1987)). Activation via the TCR provides a more physiologic model, since the cellular events following crosslinking of TCR by anti-CD3 mimic the transmembrane signaling that occurs following stimulation with antigen in association with MHC proteins. The results obtained using anti-CD3 stimulation are shown in Table 2 below for the same normal donors depicted in Table 1. Activation with anti-CD3 mAb fixed to plastic resulted in a small, 2- to 3-fold proliferative response above medium controls for the majority of donors examined. In contrast, donor 1 demonstrated a 10-fold stimulation. This increased proliferation was presumably due to the greater number of contaminating monocytes found in the preparation from this donor, as the presence of monocytes greatly increases the stimulatory potential of fixed anti-CD3 mAb (Jenkins et al, *J. Immunol.*, 140:3324–3330 (1988)). When CHO-B7 cells were added to anti-CD3-activated T cells, a marked increase in stimulation index, ranging from 23- to 180-fold, was observed. The addition of anti-CD28 mAb also led to a marked increase in proliferation, with a stimulation index ranging from 30- to 75-fold over that observed with anti-CD3 mAb alone. This stimulation appeared to be B7-specific, since CHO-mock cells did not augment proliferation. Addition of anti-B7 mAb completely blocked the proliferative response obtained with the CHO-B7 cells but again had no effect on the responses seen with anti-CD28 mAb. This further confirms that the stimulation occurred via binding of B7.

TABLE 2

Effect of anti-CD-3, anti-CD28, and CHO-B7 cells on proliferation of CD28+ T Cells

| CD28+ cell treatment | [$^3$H] Thymidine incorporation, cpm (mean ± SEM) | | |
|---|---|---|---|
| | Donor 1 | Donor 2 | Donor 3 |
| Medium control | 156 ± 65 | 130 ± 11 | 151 ± 29 |
| Anti-CD3 | 1,953 ± 631 | 245 ± 14 | 347 ± 169 |
| Anti-CD28 | 88 ± 18 | 109 ± 6 | 188 ± 6 |
| CHO-B7 | 104 ± 6 | 102 ± 9 | 143 ± 37 |
| Anti-CD3 + CHO-B7 | 46,543 ± 11,010 | 45,146 ± 4,391 | 35,106 ± 2,847 |
| Anti-CD3 + anti-CD28 | 56,836 ± 10,440 | 18,383 ± 5,334 | 26,873 ± 7,833 |
| Anti-CD3 + CHO-mock | 1,618 ± 158 | 519 ± 135 | 282 ± 7 |
| Anti-CD3 + CHO-B7 + anti-B7 | 174 ± 5 | 2,377 ± 1,072 24,290 ± | 321 ± 57 30,326 ± |
| Anti-CD3 + anti-CD28 + anti-B7 | 54,646 ± 3,932 | 14,630 | 13,853 |

G. B7-Transfected CHO Cells Induce IL-2 but Not IL-4 Secretion.

Stimulation of submitogenically activated T cells with anti-CD28 mAb has been shown to result in increased IL-2 production (Thompson et al, Proc. Natl. Acad. Sci, USA, 85:1194–1198 (1988)). To determine whether IL-2 secretion could be induced by ligation of cell surface B7, the culture supernatants from cells co-cultured with either PMA or anti-CD3 in the presence of CHO-B7 cells or anti-CD28 were collected from the above experiments and assayed for lymphokine production. Results of two representative donors from seven tested are depicted in Table 3. No IL-2 or IL-4 was detected when the CD28+ T cells were stimulated with PMA alone. When anti-CD28 mAb was added to PMA-stimulated CD28+ T cells, IL-2 secretion was markedly increased. In contrast, there was no significant increase in IL-4 secretion over background, although positive controls demonstrated sensitivity and specificity of the assay. The addition of CHO-B7 cells similarly resulted in a marked increase in IL-2 secretion but to a lesser extent, ≈45% of that observed with anti-CD28 mAb. As was observed with anti-CD28 mAb, there was no increase in IL-4 production. There was no IL-2 production when resting T cells were co-cultured with either anti-CD28 mAb or CHO-B7 cells. CHO-mock cells did not induce IL-2 secretion by PMA-stimulated CD28+ cells. The addition of anti-B7 mAb specifically and nearly completely blocked the stimulation of IL-2 production by CHO-B7 cells. The anti-B7 mAb had no effect on IL-2 production in the activated cells stimulated with anti-CD28 mAb.

Previous studies have demonstrated that the addition of PMA and the calcium ionophore ionomycin strongly stimulates proliferation of CD28+ cells (June et al, J. Immunol., 143:153–161 (1989)). Costimulation of CD28 cells with both PMA and ionomycin enhanced proliferation by up to 75-fold compared with PMA alone in seven independent experiments. When anti-CD28 mAb or CHO-B7 cells were added to PMA- and ionomycin-stimulated CD28 cells, proliferation was minimally augmented, between 1- and 2-fold. However, to determine whether B7 ligation could further enhance IL-2 production, PMA- and ionomycin-stimulated CD28 cells were co-cultured with CHO-B7 cells or anti-CD28 mAb. As seen in Table 3 below, CD28+ cells cultured with PMA and ionomycin secreted low levels of IL-2 and very low levels of IL-4. Addition of anti-CD28 mAb to the PMA-and ionomycin-stimulated cells led to maximal IL-2 production, which was only slightly greater than those levels observed when anti-CD28 mAb was added to cultures containing PMA alone. Addition of CHO-B7 cells to the PMA- and ionomycin-stimulated CD28+ cells induced higher levels of IL-2 secretion than was observed when the CHO-B7 cells were added to CD28+ cells stimulated with PMA alone. Finally, specificity for B7 was again confirmed, since anti-B7 mAb inhibited IL-2 production by 95%.

TABLE 3

Effect of B7 on IL-2 and IL-4 production in phorbol ester-stimulated CD28+ cells

| | Donor 1 | | Donor 2 | |
|---|---|---|---|---|
| CD28+ cell treatment | IL-2 pg/ml | IL-4 pg/ml | IL-2 pg/ml | IL-4 pg/ml |
| Medium control | <30 | <30 | <30 | <30 |
| PMA | <30 | <30 | <30 | <30 |
| Anti-CD28 | <30 | ND | <30 | ND |
| PMA + anti-CD28 | 10,500 | 65 | 11,300 | 60 |
| PMA + CHO-B7 | 3,800 | <30 | 5,900 | 40 |
| PMA + CHO-mock | <30 | <30 | <30 | <30 |
| PMA + CHO-B7 + anti-B7 | 80 | <30 | <30 | ND |
| PMA + anti-CD28 + anti-B7 | 9,000 | ND | 11,200 | ND |
| PMA + IM | 80 | 50 | <30 | <30 |
| PMA + IM + anti-CD28 | 11,500 | <30 | 14,500 | <30 |
| PMA + IM + CHO-B7 | 6,000 | <30 | 10,000 | ND |
| PMA + IM + CHO-B7 + anti-B7 | 340 | <30 | <30 | ND |
| PMA + IM + anti-CD28 + anti-B7 | 10,000 | ND | 7,500 | ND |

IM = ionomycin; ND = not done.

Similar results were obtained when anti-CD3 fixed to plastic was used to stimulate CD28 cells. As seen in Table 4, stimulation with anti-CD3 led to very low levels of IL-2 secretion and virtually no detectable IL-4. Addition of either anti-CD28 mAb or CHO-B7 cells led to maximal IL-2 secretion without production of IL-4. Again, anti-B7 mAb could inhibit IL-2 secretion by CHO-B7 cells but had no effect on anti-CD28 stimulation.

TABLE 4

Effect of B7 on IL-2 and IL-4 production in anti-CD3-stimulated CD28+ T cells

| | Donor 1 | | Donor 2 | |
|---|---|---|---|---|
| CD28+ cell treatment | IL-2 pg/ml | IL-4 pg/ml | IL-2 pg/ml | IL-4 pg/ml |
| Medium control | <30 | <30 | <30 | <30 |
| Anti-CD3 | 80 | <30 | <30 | 45 |
| Anti-CD3 + anti-CD28 | 1500 | <30 | 1350 | <30 |
| Anti-CD3 + CHO-B7 | 1050 | <30 | 1350 | 40 |

TABLE 4-continued

Effect of B7 on IL-2 and IL-4 production in
anti-CD3-stimulated CD28+ T cells

|  | Donor 1 | | Donor 2 | |
| --- | --- | --- | --- | --- |
| CD28+ cell treatment | IL-2 pg/ml | IL-4 pg/ml | IL-2 pg/ml | IL-4 pg/ml |
| Anti-CD3 + CHO-mock | <30 | <30 | <30 | <30 |
| Anti-CD3 + CHO-B7 + anti-B7 | 130 | <30 | <30 | ND |
| Anti-CD3 + anti-CD28 + anti-B7 | 2200 | <30 | 1500 | ND |

ND = not done.

EXAMPLE 8

This example describes the molecular cloning and characterization of a murine homologue of the human B7 activation antigen.

Isolation of murine cDNA clones. In preliminary experiments, low stringency hybridization of the human B7 cDNA insert (Freeman et al, *J. Immunol.*, 143:2714 (1989)) to blots of poly(A)+ RNA from the murine B cell lines 70Z, A20, TA3, and NS-1 suggested the presence of cross-hybridizing mRNAs in 70Z and A20. The $^{32}$P-labeled, 1.5 kb human B7 cDNA insert was used to screen a lambda gt11 cDNA library generated from the mouse pre-B cell line, 70Z/3 (Ben-Neriah et al, *Cell*, 44:577 (1986)). Hybridization at reduced stringency was performed in 5×SSPE, 5×Denhardt's solution, 0.2% SDS, 50µg/ml salmon sperm DNA at 50° C. Final washes were in 2×SSC, 0.1% SDS at 52.5° C. for 20 min. A single cDNA clone was isolated and the cDNA insert isolated by digestion with EcoRI followed by agarose gel purification. DNA sequence analysis of the cDNA from 70Z revealed that it was composed of 1180 bases of intron followed by a splice aceptor and that it contained a region homologous to the human B7 Ig-C, transmembrane, cytoplasmic, and 3' untranslated domains but was an incomplete cDNA because it lacked the 5' untranslated, signal peptide and IgV domains. A DNA fragment containing the Ig-C, transmembrane, and cytoplasmic domains was generated by polymerase chain reaction using the cDNA as a template with a sense primer of GCTGACTTCTCTACCC and an anti-sense primer of CTAAAGGAAGACGGTCT. The PCR amplification was performed using Taq polymerase. Twenty cycles of 94°, 1 min., 44°, 1 min., 72°, 1 min., and a final extension cycle of 72°, 10 min., were performed. The PCR product was gel purified and used to screen a cDNA library prepared from the mouse B cell line, A20, in the pCDM8 vector under stringent conditions. Hybridation at high stringency was conducted using the same buffer but at 65° C. Final washes were in 0.2×SSCS at 65° C. Four additional cDNA clones were isolated. The cDNA insert of one of these was isolated by digestion with XbaI followed by agarose gel purification. The cDNA insert was ligated into XbaI digested pSKII-. DNA sequence analysis revealed that the cDNA insert contained a region homologous to human B7 5' untranslated, signal peptide, Ig-V, and Ig-C domains but was incomplete because it lacked the transmembrane, cytoplasmic, and 3' untranslated domains. The Ig-C region was identical between the two murine cDNA clones and contained a convenient BamHI restriction enzyme site facilitating their ligation together. A complete murine B7 cDNA clone was constructed as follows: The first (from 70Z) cDNA clone was ligated into the EcoRI site of the eukaryotic expression vector, pcDNAI (Invitrogen, San Diego, Calif.), followed by digestion with BamHI, and purification of the large fragment containing the PcDNAI vector and the Ig-C, transmembrane, cytoplasmic, and 3' untranslated domains. The second cDNA clone (from A20) in the pSKII- vector, was digested with BamHI and the fragment containing the mB7 5' untranslated, signal peptide, Ig-V, and Ig-C domains was isolated by agarose gel electrophoresis and ligated to the BamHI fragment containing the pcDNAI vector and the Ig-C, transmembrane, cytoplasmic, and 3' untranslated domains from the 70Z cDNA clone. This generated a complete murine B7 cDNA clone. Subsequently, a second murine B7 cDNA clone from the A20 library was sequenced and found to have a sequence identical to the one generated by ligating the two incomplete cDNAs together.

DNA sequence analysis. B7 cDNA inserts were subcloned into the pKSII plasmid (Stratagene, La Jolla, Calif.). Nested deletions were constructed using the Erase-A-Base kit according to the manufacturer's directions (Promega, Madison, Wis.). Single stranded phagemid DNA was prepared by M13k07 helper virus infection as described (*Methods In Enzymology*, 153:3–34 (1987)) and used as the sequencing template. The cDNA insert was sequenced using dye labelled primers and Taq polymerase (Applied Biosystems, Foster City, Calif.) and the sequencing reactions were analyzed on an Applied Biosystems model 373 automated fluorescent sequencer. Sequence data obtained from overlapping deletion clones on both strands were assembled to yield the final murine B7 sequence illustrated in SEQ ID NO:3. Sequencing analysis and database comparisons employed both GCG (Genetics Computer Group, Madison, Wis.) and IG-Suite (Intelligenetics, Mountain View, Calif.) programs and databases.

A search of the Genbank and EMBL databases with the murine B7 nucleotide sequence revealed that only the human B7 sequence exhibited significant homology with the murine sequence (sigma=24 standard deviations above the mean). Comparison of the murine B7 cDNA sequence with that of human B7 showed that the two were 60% identical. Homologous domains include the 5' (50%) and 3' (40%) untranslated regions in addition to the protein coding sequence (63%). A poly(A) tract following a consensus polyadenylation signal (bases 1678–1683) was identified.

Analysis of the murine B7 cDNA reveals a single, long open reading frame of 942 bases initiated by one of three closely spaced ATG codons beginning at nucleotides 225, 249, and 270 and ending at nucleotide 1166. The second of these ATG codons was chosen (nt 249) as the initiating methionine because the DNA sequence GCTATGG around this ATG is consistent with the consensus translation initiation sequence RCCATGG defined by Kozak (Kozak, *Nucleic Acids Res.*, 15:8125 (1987)). In addition, the region 5' of this ATG is highly similar (15 of 17 nucleotides identical) to the human start site. Initiation at this methionine predicts an open reading frame of 918 bases encoding a protein of 306 amino acids.

FIG. 4 shows the alignment of the murine and human B7 protein sequences and the structural features associated with these molecules. The structural domains shown for murine B7 are based on a comparison with human B7 and with other members of the Ig supergene family. The initiatory methionine codon is followed by a 37 amino acid signal peptide. The length of the signal peptide was chosen to correspond to the signal cleavage site experimentally determined for human B7 expressed in CHO cells. Amino terminal sequencing of a soluble human B7 purified from the culture media of transfected CHO cells revealed that the mature human B7 began with the amino acid sequence valine—isoleucine—histidine—valine (see Example 6 herein).

Hydrophobicity analysis reveals that the putative signal sequence agrees with the profile for a consensus signal peptide and that a highly hydrophobic membrane spanning domain is located at amino acids 211–235. Ig-V (amino acids 1–105) and Ig-C (amino acids 106–199) domains retain many of the conserved amino acids important for the structure of the Ig supergene family (Williams et al, *Ann. Rev. Immunol.*, 6:381 (1988)). The complete human and murine B7 protein sequences were 44% identical with 47% identity in the Ig-V domain and 57% in the Ig-C domain. The murine B7 transmembrane domain contains two cysteine residues, as opposed to three in human B7, and these could be involved in lipid derivatization or covalent interaction with other membrane proteins. The murine B7 cytoplasmic domain is not closely related to its human counterpart but retains its highly charged nature. Both murine and human B7 contain eight potential N-linked glycosylation sites of which four are conserved between the two sequences. Three of the common glycosylation sites were found in the Ig-C domain and one in the Ig-V domain. The murine and human B7 proteins differ in that the murine B7 exhibits an Ig hinge-like region between the Ig-C and transmembrane domains. This should confer greater flexibility to the murine B7. The predicted mature murine B7 protein would contain 269 amino acids with a molecular weight of 30386 daltons as opposed to 254 amino acids and 29311 for human B7. Glycosylation of the human B7 protein leads to an apparent molecular weight of 44–54 Kd and a similar increase would be expected for murine B7.

A search of the PIR (Protein Identification Resource) and the Swiss-Prot (Intelligenetics) protein databases with the murine B7 protein sequence revealed similarities with several immunoglobulin variable and constant domains of human and murine origins. Human B7 was not found in the protein homology searches because this sequence was not present in the databases searched. However, searching all three reading frame translations of the Genbank and EMBL databases with the murine B7 protein sequence showed that homology with human B7 is much greater than all other sequences.

Expression of Murine B7 RNA

In this example, the murine B7 clone was used to characterize the lineage restriction of murine B7.

B7 Hybridization probe. A DNA fragment corresponding to the protein coding region of the murine B7 cDNA was used as a probe for RNA and DNA blot hybridizations because of the presence of a repetitive element in the 3' untranslated region of the B7 mRNA. The complete murine B7 cDNA was used as a template for PCR amplification of the coding region using a sense primer (ATGGCTTGCAATTGTCAG) and anti-sense primer (CTAAAGGAAGACGGTCT) corresponding to nucleotides 249–266 and 1169–1153 of the cDNA sequence. The 921 bp coding region PCR product was gel purified and used in DNA and RNA blot hybridization in accordance with standard techniques.

Briefly, RNA was prepared from various organs isolated from a 4 week old Balb/c mouse. RNA was also prepared from the murine pre-B cell lines 38B9 and 300.19, the B cell lymphomas AJ9, CH1 and A20, the plasmacytoma lines, Ag8.653 (P3×63-Ag8.653) and NS-1 (P3/NS1/1-Ag4-1), the T cell lymphoma lines, EL4, BW5147, and YAC, and the thymoma line RADA. RNA preparation, detailed characterizations, and sources of these cells are as described (Zhou et al, "Structure and domain organization of the CD19 antigen of human, mouse and guinea pig B lymphocytes: Conservation of the extensive cytoplasmic domain", *J. Immunol.*, (in press)). Two micrograms of poly(A)$^+$ RNA were denatured with glyoxyl, electrophoresed on an agarose gel, and blotted onto nitrocellulose membranes (Schleicher and Schuell, Keene, NH).

Figure 2A:
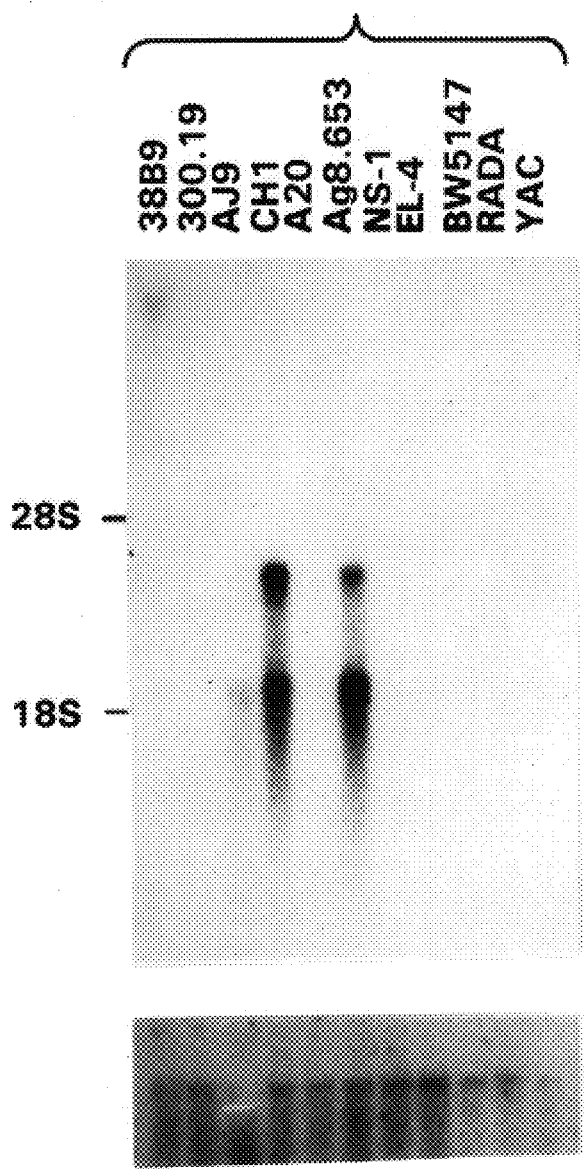
FIGS. 2A–B is an RNA blot analysis illustrating that murine B7 mRNA expression is B cell restricted. RNA blot analysis of (A) lymphoid cell lines and (B) Balb/c mouse organs is shown. Two micrograms of poly(A)$^+$ RNA were glyoxylated, electrophoresed on agarose gels and transferred to nitrocellulose. The blot was hybridized with (a)$^{32}$P-labeled mB7 coding region cDNA and reprobed with (b) $^{32}$P labeled rat actin cDNA. The lanes contain RNA from the murine pre-B cell lines, 38B9 and 300.19, the B cell lines, AJ9, CH1, and A20, the plasmacytoma lines, Ag8.653 and NS-1, and the T cell lines, EL-4, BW5147, RADA, and YAC. The mobility of rRNAs are indicated on the left.

The DNA fragment corresponding to the protein coding region of the murine B7 cDNA (base pairs 249–1169) was synthesized using PCR because of the presence of a repetitive element in the 3' untranslated region of the B7 mRNA. Using this B7 coding region probe, RNA blot hybridization analysis of B7 mRNA expression in murine lymphoid cells revealed that B7 was expressed in the mature B cell lines AJ9 and CH1, in the plasmacytoma line Ag8.653 and at low levels in the mature B cell line A20 (FIG. 2A). Two mRNA transcripts of 2.2 and 3.9 Kb were detected in poly(A)$^+$ RNA. This is a more simple transcript pattern than seen in human B cell lines where transcripts of 1.7, 2.9, 4.2, and 10 Kb were detected. A large transcript (approx. 10 Kb) was observed in the pre-B cell line 38B9. B7 mRNA expression was not detected in the pre-B cell line 300.19, the plasmacytoma line NS-1, or the T cell lines EL-4, BW5147, RADA, and YAC.

Figure 2B:
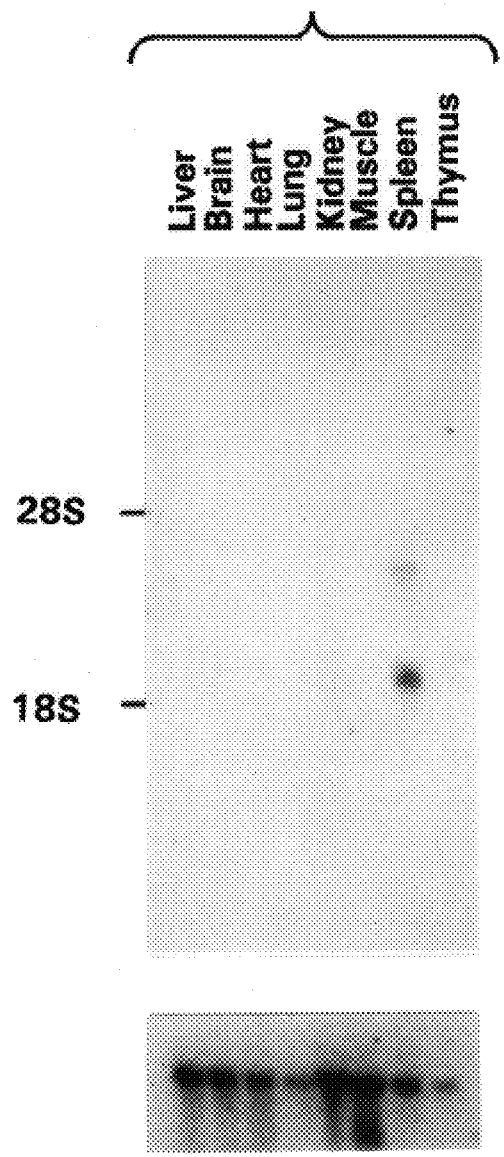

RNA blot hybridization analysis of poly(A)$^+$ RNA isolated from murine organs demonstrated that B7 expression was restricted to murine splenocytes (FIG. 2B). No expression was observed in liver, brain, heart, lung, kidney, muscle, or thymus. In both murine splenocytes and B cell lines, 2.2 and 3.9 Kb mRNA transcripts were identified, with the 2.2 Kb transcript predominating. Thus, B7 expression is restricted in both murine and human lymphoid cells to mature B cells, some pre-B and plasmacytoma cell lines, but is not found in T cell lines.

DNA Blot Hybridization Analysis

Figure 3:
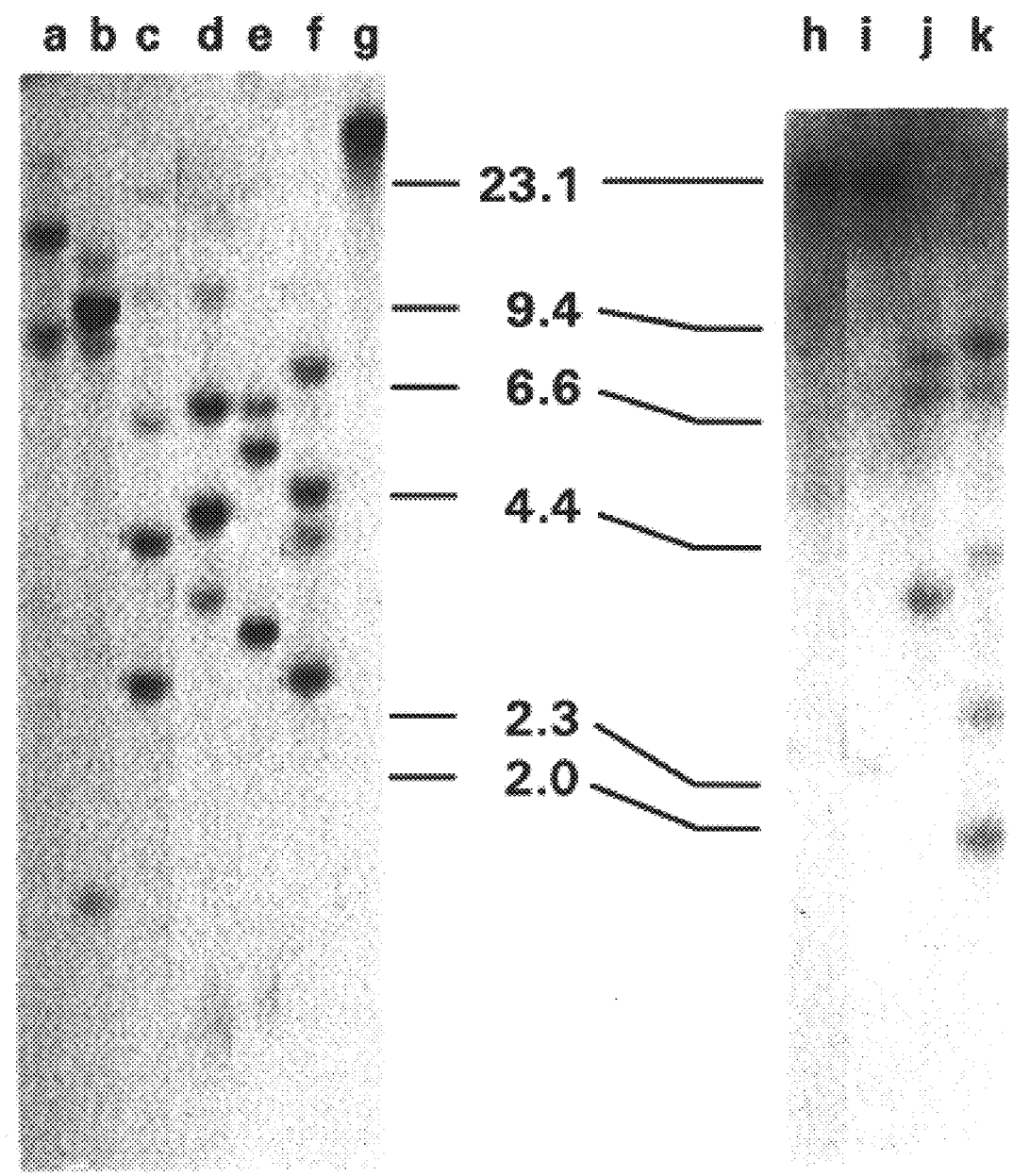
FIG. 3 is a genomic DNA blot analysis of B7. Five micrograms of C57BL/6 splenic DNA were digested with (a)BamHI, (b)EcoRI, (c)BclI, (d)KpnI, (e)BglII, (f)XbaI, (g)EcoRV, (h)ApaI, (i)BglI, (j)BstXI, and (k)SacI. DNAs were electrophoresed in 0.7% agarose, blotted, and hybridized with $^{32}$P-labeled mB7 coding region cDNA. The sizes, in kb, of molecular weight markers are indicated.

DNA blot analysis to determine the genomic organization of B7 was performed using the B7 coding region described in FIG. 3. Isolation of genomic DNA and DNA blot hybridizations were performed as described (Maniatis et al, "Molecular Cloning: A laboratory manual", Cold Spring Harbor Laboratory, Cold Spring Harbor, N.Y. (1989)). The 921 bp murine B7 coding region PCR product and the actin cDNA insert were labelled by random oligonucleotide priming using $\alpha$-$^{32}$P-labeled dCTP and the Klenow fragment of DNA polymerase. Hybridization, washing, and autoradiography were performed as previously described (Freeman et al, *J. Immunol.*, 143:2714 (1989); Maniatis et al, "Molecular Cloning: A laboratory manual", Cold Spring Harbor Laboratory, Cold Spring Harbor, N.Y.).

Five micrograms of C57BL/6 splenic DNA were digested with eleven different restriction endonucleases: (a) BamHI, (b) EcoRI, (c) BclI, (d) KpnI, (e) BglII, (f) XbaI, (g) EcoRV, (h) ApaI, (i) BglI, (j) BstXI and (k) SacI. DNA's were electrophoresed in 0.7% agarose, blotted and hybridized with $^{32}$P-labeled mB7 coding region cDNA. The sizes, in kb, of molecular weight markers, are indicated in FIG. 3. When genomic DNA was digested with the eleven different restriction endonucleases, the B7 coding region probe hybridized to between one and five restriction enzyme fragments. Digestion with ApaI or EcoRV produced a single DNA fragment, consistent with a single copy of the B7 gene per haploid genome. Digestion with SacI or BclI, which are not present in the B7 coding region, each produced 5 DNA fragments. These results suggest that the murine B7 protein coding region encompasses approximately 20 Kb and is divided into at least 5 exons. If these correspond to the human B7 genomic organization, these will encode the signal peptide, Ig-V, Ig-C, transmembrane, and cytoplasmic domains.

EXAMPLE 9

This Example demonstrates that murine B7 is costimulatory for human CD28+ T cells, suggesting the existence of a highly conserved binding domain.

*Cells.* Human CD28+ T cells were isolated from peripheral blood mononuclear cells as described (Gimmi et al, "B7 provides a costimulatory signal which induces T cells to proliferate and secrete interleukin-2", *Proc. Natl. Acad. Sci. USA*, (in press)).

*Monoclonal antibodies.* 4B10 (IgG1) is an anti-CD28 mAb (Gimmi et al). Optimal stimulation of T cells with anti-CD28 mAb was obtained at a concentration of 1 µg/ml and this dose was used throughout the experiments. 4B10 was purified using a protein A Sepharose column (Bio-Rad) as described (Gimmi et al). The anti-B7 mAb, 133, (IgM) was characterized in our laboratory (Freeman et al, *J. Immunol.*, 143:2714 (1989); Freedman et al, *J. Immunol.*, 137:3260 (1987)) and was used at a final concentration of 10 µg/ml.

B7-Transfection. Transient expression of B7 cDNA clones in COS cells was performed as previously described (Aruffo et al, *Proc. Natl. Acad. Sci. USA*, 84:8573 (1987)). COS cells transfected with the PcDNAI vector alone were also prepared. Transfected COS cells were used 72 hrs. after the addition of DNA. A stably transfected CHO cell line expressing human B7 was constructed as previously described and is referred to as CHO-hB7 (Gimmi et al).

Cell-fixation. COS and CHO cells were detached from tissue culture plates and fixed with paraformaldehyde as described in Example 7.

Proliferation assay. The capacity of B7 to costimulate T cell proliferation was measured as described in Example 7. Briefly, human CD28+ T lymphocytes were stimulated with phorbol myristate 13-acetate (PMA) (Calbiochem, La Jolla, Calif.) at 1 ng/ml final concentration (June et al, *J. Immunol.*, 143:153 (1989)). The fixed CHO-hB7 and COS cell transfectants were added at a concentration of $2 \times 10^4$ cells/well. The specificity of the stimulation with COS-hB7 cell was assayed by the addition of anti-B7 mAb to the cultures at a final concentration of 10 µg/ml. The cells were pulsed with 1 µCi of $^3$H-thymidine (ICN Flow, Costa Mesa, Calif.) during the last eight hours of a 72 hour culture, harvested onto filters, and counted.

Table 1 below summarizes one of three representative experiments. Coincubation of paraformaldehyde fixed COS-mB7 or COS-hB7 cells with PMA treated CD28+ human T cells resulted in 29 fold and 30 fold enhancement of proliferation, respectively, compared to T cells treated with PMA alone. Addition of anti-HB7 mAb could completely inhibit the costimulatory activity of COS-hB7 cells but not of COS-mB7 cells. Addition of paraformaldehyde fixed CHO-hB7 transfected cells resulted in a 51 fold increase in proliferation. In contrast, coincubation of PMA treated T cells with paraformaldehyde fixed COS-Vector resulted in no increase in proliferation. Paraformaldehyde fixed CHO-hB7, COS-hB7, COS-mB7 and COS vector transfected cells did not induce untreated human CD28+ cells to proliferate above media control.

TABLE 1

Effect of murine and human B7 expressing cells on the proliferation of phorbol ester treated human CD28+ T cells

| | cmp ± SEM |
|---|---|
| Human CD28+ T cells co-cultured with: | |
| media | 148 ± 18 |
| PMA | 689 ± 48 |

TABLE 1-continued

Effect of murine and human B7 expressing cells on the proliferation of phorbol ester treated human CD28+ T cells

| | cmp ± SEM |
|---|---|
| anti-CD28 | 109 ± 17 |
| CHO-hB7 | 70 ± 2 |
| COS-hB7 | 47 ± 7 |
| COS-mB7 | 40 ± 4 |
| COS-Vector | 89 ± 28 |
| PMA + anti-CD28 | 58646 ± 3093 |
| PMA + CHO-hB7 | 34910 ± 982 |
| PMA + COS-hB7 | 20676 ± 897 |
| PMA + COS-mB7 | 200081 ± 1516 |
| PMA + COS-Vector | 392 ± 34 |
| PMA + COS-hB7 + anti-hB7 | 356 ± 52 |
| PMA + COS-mB7 + anti-hB7 | 17395 ± 1367 |

EXAMPLE 10

Construction of a B7 "knock out" mouse

A DNA fragment corresponding to the protein coding region of the murine B7 cDNA is used as a probe for hybridizations because of the presence of a repetitive element in the 3' untranslated region of the B7 mRNA. The complete murine B7 cDNA is used as a template for PCR amplification of the coding region using a sense primer (ATGGCTTGCAATTGTCAG) and anti-sense primer (CTAAAGGAAGACGGTCT) corresponding to nucleotides 249–266 and 1169–1153 of SEQ ID NO:3. The PCR amplification is performed using Taq polymerase. Twenty cycles of 94°, 1 min., 44°, 1 min., 72°, 1.5 min., and a final extension cycle of 72°, 10 min., are performed. The 921 bp coding region PCR product is gel purified and used for all blot hybridizations.

The genomic region encoding the mB7 gene is isolated by using the 921 bp coding region PCR product to screen a lambda murine genomic DNA library. A 12 kb BamHI DNA fragment containing the mB7 IgV and IgC exons is ligated into BamHI digested pSKII-. A B7 "knock out" plasmid is constructed as follows: The protein coding sequence of the mB7 IgV exon is disrupted by the insertion of a DNA fragment containing the phosphoglycerate kinase promoter and neomycin resistance gene into the PvuII site in the mB7 IgV exon. The 15 kb plasmid containing the mB7 IgV and IgC exons is partially digested with PvuII and a 15 kb linear molecule is isolated by gel electrophoresis. The phosphoglycerate kinase promoter and neomycin resistance gene are isolated from the pKJ-Neo plasmid by digestion with XhoI and SalI, followed by gel electro-phoresis. The fragment is rendered blunt ended by treatment with Klenow fragment of DNA polymerase and ligated into the PvuII site in the mB7 IgV exon. A DNA fragment containing the Thymidine kinase gene is isolated from the pMC1-TK plasmid by digestion with PstI and HindIII, followed by gel electro-phoresis. The 17 kb plasmid containing the phosphoglycerate kinase promoter and neomycin resistance gene in the PvuII site of the mB7 IgV exon is digested with Hind III and partially digested with PstI. A 14 kb fragment is isolated and ligated with the PstI and HindIII digested thymidine kinase gene. This plasmid is linearized by digestion with PvuI and introduced into murine embryonal stem (ES) cells by electroporation. ES cells containing the plasmid are isolated by selection in 400 µg/ml G418. Cells are characterized for correct insertion of mB7 into the mB7 gene by hybridization. ES cells with a targeted mouse B7 insertion are introduced into murine embryos in accordance with established techniques. After birth, these mice are characterized for the presence of the B7 "knock out" plasmid by hybridization. Mice containing the B7 "knock out" are bred and will be characterized for their ability to accept grafts, reject tumors, and defend against infectious diseases.

Having described the invention, what is claimed is:

1. An isolated nucleic acid molecule comprising a nucleotide sequence coding for a portion of the B7 polypeptide set forth in SEQ ID NO:2, wherein the portion is the extracellular domain of said polypeptide.

2. A vector comprising a nucleic acid molecule according to claim 1.

3. A host cell transformed by a vector according to claim 2.

4. An isolated nucleic acid molecule according to claim 1, wherein the portion consists of amino acids 1–208.

5. An isolated nucleic acid molecule comprising a nucleotide sequence encoding the amino acid sequence set forth in SEQ ID NO:2.

6. A vector comprising a nucleic acid molecule according to claim 5.

7. A host cell transformed by a vector according to claim 6.

8. An isolated nucleic acid molecule comprising a nucleotide sequence encoding the amino acid sequence set forth in SEQ ID NO: 4.

9. An isolated nucleic acid molecule comprising the nucleotide sequence set forth in SEQ ID NO:1.

10. A vector comprising a nucleic acid molecule according to claim 9.

11. A vector comprising the nucleic acid molecule of claim 9 in which the vector is a viral vector.

12. An isolated nucleic acid molecule comprising the nucleotide sequence set forth in SEQ ID NO:3.

13. An isolated nucleic acid molecule comprising a nucleotide sequence coding for a portion of the B7 polypeptide set forth in SEQ ID NO:2, wherein the portion consists of amino acids 1–254.

14. A vector comprising a nucleic acid molecule according to claim 13.

15. A vector comprising the nucleic acid molecule of claim 13 in which the vector is a viral vector.

16. An isolated nucleic acid molecule comprising a nucleotide sequence coding for a portion of the B7 polypeptide set forth in SEQ ID NO:2, wherein the portion consists of amino acids 209–235.

17. An isolated nucleic acid molecule comprising a nucleotide sequence coding for a portion of the B7 polypeptide set forth in SEQ ID NO:2, wherein the portion consists of amino acids 1–235.

18. An isolated nucleic acid molecule comprising a nucleotide sequence coding for a portion of the B7 polypeptide set forth in SEQ ID NO:2, wherein the portion consists of amino acids 236–254.

19. An isolated nucleic acid molecule comprising a nucleotide sequence coding for a portion of the B7 polypeptide set forth in SEQ ID NO:2, wherein the portion consists of amino acids 209–254.

20. An isolated nucleic acid molecule comprising a nucleotide sequence coding for a portion of the B7 polypeptide, said nucleic acid comprising nucleotides 318 to 1181 of SEQ ID NO:1.

21. A vector comprising a nucleic acid molecule according to claim 20.

22. A vector comprising the nucleic acid molecule of claim 20 in which the vector is a viral vector.

23. An isolated nucleic acid molecule coding for a portion of the B7 polypeptide set forth in SEQ ID NO: 2, wherein the portion comprises an IgV-like domain.

24. An isolated nucleic acid molecule coding for a portion of the B7 polypeptide set forth in SEQ ID NO: 2 wherein the portion comprises an IgC-like domain.

25. An isolated nucleic acid molecule comprising a nucleotide sequence encoding the amino acid sequence set forth in SEQ ID NO: 2 operably linked to a regulatory sequence.

26. An isolated nucleic acid molecule comprising a nucleotide sequence encoding amino acids 1–254 of the amino acid sequence set forth in SEQ ID NO: 2 operably linked to a regulatory sequence.

27. An isolated nucleic acid molecule consisting of a nucleotide sequence which encodes the amino acid sequence set forth in SEQ ID NO:2.

28. A vector comprising the nucleic acid molecule of claim 27 in which the vector is a viral vector.

29. An isolated nucleic acid molecule encoding a B7 polypeptide comprising the amino acid sequence set forth in SEQ ID NO:4.

30. An isolated nucleic acid molecule comprising a nucleotide sequence encoding a B7 polypeptide wherein said nucleotide sequence hybridizes with the nucleotide sequence of SEQ ID NO:1 or SEQ ID NO:3 under the conditions of 5× SSPE, 5× Denhart's solution, 0.2% SDS, 50 µg/ml salmon sperm DNA at 50° C., with final washes in 2×SSC containing 0.1% SDS at 52.5° C.

31. The nucleic acid molecule of claim 30, which is of human origin.

32. The nucleic acid molecule of claim 30, which is of mouse origin.

33. The nucleic acid molecule of claim 30, which encodes a polypeptide which comprises the B7 extracellular domain set forth in SEQ ID NO:2.

34. The nucleic acid molecule of claim 30, which encodes a polypeptide which comprises the B7 extracellular domain set forth in SEQ ID NO:4.

35. A nucleic acid molecule which encodes a soluble B7 molecule comprising amino acids 1–204 of SEQ ID NO:2.

36. A nucleic acid molecule which encodes a soluble B7 molecule consisting of amino acids 1–204 or of SEQ ID NO:2.

37. A nucleic acid molecule which encodes a soluble B37 molecule comprising amino acids −34–204 of SEQ ID NO:2.

38. A nucleic acid molecule which encodes a soluble B7 molecule consisting of amino acids −34–204 of SEQ ID NO:2.

* * * * *

```
                              SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 1491 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: no (iv) ANTI-SENSE: no (vi) ORIGINAL SOURCE:
         (A) ORGANISM: Homo sapien
         (F) TISSUE TYPE: lymphoid
         (G) CELL TYPE: B cell
         (H) CELL LINE: Raji (vii) IMMEDIATE SOURCE:
         (A) LIBRARY: cDNA in pCDM8 vector
         (B) CLONE: B7, Raji clone #13

(viii) POSITION IN GENOME:
         (A) CHROMOSOME/SEGMENT: 3

(ix) FEATURE:
         (A) NAME/KEY:  Open reading frame (translated region)
         (B) LOCATION:  318 to 1181 bp
         (C) IDENTIFICATION METHOD: similarity to other pattern (ix) FEATURE:
         (A) NAME/KEY:  Alternate polyadenylation signal
         (B) LOCATION:  1474 to 1479 bp
         (C) IDENTIFICATION METHOD: similarity to other pattern (x) PUBLICATION INFORMATION:
         (A) AUTHORS: FREEMAN, GORDON J.
             FREEDMAN, ARNOLD S.
             SEGIL, JEFFREY M.
             LEE, GRACE
             WHITMAN, JAMES F.
             NADLER, LEE M.
         (B) TITLE:  B7, A New Member Of The Ig Superfamily With
             Unique Expression On Activated And Neoplastic B Cells
         (C) JOURNAL: The Journal of Immunology
         (D) VOLUME: 143
         (E) ISSUE: 8
         (F) PAGES: 2714-2722
         (G) DATE: 15-OCT-1989
         (H) RELEVANT RESIDUES IN SEQ ID NO:1: FROM 1 TO 1491

(xi) SEQUENCE DESCRIPTION: SEQ ID NO:1:

CCAAAGAAAA AGTGATTTGT CATTGCTTTA TAGACTGTAA GAAGAGAACA TCTCAGAAGT      60

GGAGTCTTAC CCTGAAATCA AAGGATTTAA AGAAAAAGTG GAATTTTTCT TCAGCAAGCT     120

GTGAAACTAA ATCCACAACC TTTGGAGACC CAGGAACACC CTCCAATCTC TGTGTGTTTT     180

GTAAACATCA CTGGAGGGTC TTCTACGTGA GCAATTGGAT TGTCATCAGC CCTGCCTGTT     240

TTGCACCTGG GAAGTGCCCT GGTCTTACTT GGGTCCAAAT TGTTGGCTTT CACTTTTGAC     300

CCTAAGCATC TGAAGCC ATG GGC CAC ACA CGG AGG CAG GGA ACA TCA CCA TCC    353
```

```
                Met Gly His Thr Arg Arg Gln Gly Thr Ser Pro Ser
                            -30                     -25
AAG TGT CCA TAC CTG AAT TTC TTT CAG CTC TTG GTG CTG GCT GGT CTT      401
Lys Cys Pro Tyr Leu Asn Phe Phe Gln Leu Leu Val Leu Ala Gly Leu
        -20                 -15                 -10

TCT CAC TTC TGT TCA GGT GTT ATC CAC GTG ACC AAG GAA GTG AAA GAA      449
Ser His Phe Cys Ser Gly Val Ile His Val Thr Lys Glu Val Lys Glu
    -5                   1                   5                  10

GTG GCA ACG CTG TCC TGT GGT CAC AAT GTT TCT GTT GAA GAG CTG GCA      497
Val Ala Thr Leu Ser Cys Gly His Asn Val Ser Val Glu Glu Leu Ala
                15                  20                  25

CAA ACT CGC ATC TAC TGG CAA AAG GAG AAG AAA ATG GTG CTG ACT ATG      545
Gln Thr Arg Ile Tyr Trp Gln Lys Glu Lys Lys Met Val Leu Thr Met
            30                  35                  40

ATG TCT GGG GAC ATG AAT ATA TGG CCC GAG TAC AAG AAC CGG ACC ATC      593
Met Ser Gly Asp Met Asn Ile Trp Pro Glu Tyr Lys Asn Arg Thr Ile
        45                  50                  55

TTT GAT ATC ACT AAT AAC CTC TCC ATT GTG ATC CTG GCT CTG CGC CCA      641
Phe Asp Ile Thr Asn Asn Leu Ser Ile Val Ile Leu Ala Leu Arg Pro
    60                  65                  70

TCT GAC GAG GGC ACA TAC GAG TGT GTT GTT CTG AAG TAT GAA AAA GAC      689
Ser Asp Glu Gly Thr Tyr Glu Cys Val Val Leu Lys Tyr Glu Lys Asp
75                  80                  85                  90

GCT TTC AAG CGG GAA CAC CTG GCT GAA GTG ACG TTA TCA GTC AAA GCT      737
Ala Phe Lys Arg Glu His Leu Ala Glu Val Thr Leu Ser Val Lys Ala
                95                  100                 105

GAC TTC CCT ACA CCT AGT ATA TCT GAC TTT GAA ATT CCA ACT TCT AAT      785
Asp Phe Pro Thr Pro Ser Ile Ser Asp Phe Glu Ile Pro Thr Ser Asn
            110                 115                 120

ATT AGA AGG ATA ATT TGC TCA ACC TCT GGA GGT TTT CCA GAG CCT CAC      833
Ile Arg Arg Ile Ile Cys Ser Thr Ser Gly Gly Phe Pro Glu Pro His
        125                 130                 135

CTC TCC TGG TTG GAA AAT GGA GAA GAA TTA AAT GCC ATC AAC ACA ACA      881
Leu Ser Trp Leu Glu Asn Gly Glu Glu Leu Asn Ala Ile Asn Thr Thr
    140                 145                 150

GTT TCC CAA GAT CCT GAA ACT GAG CTC TAT GCT GTT AGC AGC AAA CTG      929
Val Ser Gln Asp Pro Glu Thr Glu Leu Tyr Ala Val Ser Ser Lys Leu
155                 160                 165                 170

GAT TTC AAT ATG ACA ACC AAC CAC AGC TTC ATG TGT CTC ATC AAG TAT      977
Asp Phe Asn Met Thr Thr Asn His Ser Phe Met Cys Leu Ile Lys Tyr
                175                 180                 185

GGA CAT TTA AGA GTG AAT CAG ACC TTC AAC TGG AAT ACA ACC AAG CAA     1025
Gly His Leu Arg Val Asn Gln Thr Phe Asn Trp Asn Thr Thr Lys Gln
            190                 195                 200

GAG CAT TTT CCT GAT AAC CTG CTC CCA TCC TGG GCC ATT ACC TTA ATC     1073
Glu His Phe Pro Asp Asn Leu Leu Pro Ser Trp Ala Ile Thr Leu Ile
        205                 210                 215

TCA GTA AAT GGA ATT TTT GTG ATA TGC TGC CTG ACC TAC TGC TTT GCC     1121
Ser Val Asn Gly Ile Phe Val Ile Cys Cys Leu Thr Tyr Cys Phe Ala
    220                 225                 230

CCA AGA TGC AGA GAG AGA AGG AGG AAT GAG AGA TTG AGA AGG GAA AGT     1169
Pro Arg Cys Arg Glu Arg Arg Arg Asn Glu Arg Leu Arg Arg Glu Ser
235                 240                 245                 250

GTA CGC CCT GTA    TAACAGTGTC CGCAGAAGCA AGGGGCTGAA AAGATCTGAA      1221
Val Arg Pro Val

GGTAGCCTCC GTCATCTCTT CTGGGATACA TGGATCGTGG GGATCATGAG GCATTCTTCC   1281

CTTAACAAAT TTAAGCTGTT TTACCCACTA CCTCACCTTC TTAAAAACCT CTTTCAGATT   1341

AAGCTGAACA GTTACAAGAT GGCTGGCATC CCTCTCCTTT CTCCCCATAT GCAATTTGCT   1401
```

```
TAATGTAACC TCTTCTTTTG CCATGTTTCC ATTCTGCCAT CTTGAATTGT CTTGTCAGCC    1461

AATTCATTAT CTATTAAACA CTAATTTGAG                                      1491
```

(2) INFORMATION FOR SEQ ID NO:2:

(i) SEQUENCE CHARACTERISTICS:
        (A) LENGTH: 288 amino acids
        (B) TYPE: amino acid
        (C) TOPOLOGY: linear (ii) MOLECULE TYPE: protein
        (A) DESCRIPTION: B cell activation antigen; natural ligand
            for CD28 T cell surface antigen; transmembrane protein (ix) FEATURE:
        (A) NAME/KEY: signal sequence
        (B) LOCATION: -34 to -1
        (C) IDENTIFICATION METHOD: amino terminal sequencing of
            soluble protein
        (D) OTHER INFORMATION: hydrophobic (ix) FEATURE:
        (A) NAME/KEY: extracellular domain
        (B) LOCATION: 1 to 208
        (C) IDENTIFICATION METHOD: similarity with known
            sequence (ix) FEATURE:
        (A) NAME/KEY: transmembrane domain
        (B) LOCATION: 209 to 235
        (C) IDENTIFICATION METHOD: similarity with known
            sequence (ix) FEATURE:
        (A) NAME/KEY: intracellular domain
        (B) LOCATION: 236 to 254
        (C) IDENTIFICATION METHOD: similarity with known
            sequence (ix) FEATURE:
        (A) NAME/KEY: N-linked glycosylation
        (B) LOCATION: 19 to 21
        (C) IDENTIFICATION METHOD: similarity with known
            sequence (ix) FEATURE:
        (A) NAME/KEY: N-linked glycosylation
        (B) LOCATION: 55 to 57
        (C) IDENTIFICATION METHOD: similarity with known
            sequence (ix) FEATURE:
        (A) NAME/KEY: N-linked glycosylation
        (B) LOCATION: 64 to 66
        (C) IDENTIFICATION METHOD: similarity with known
            sequence (ix) FEATURE:
        (A) NAME/KEY: N-linked glycosylation
        (B) LOCATION: 152 to 154
        (C) IDENTIFICATION METHOD: similarity with known
            sequence (ix) FEATURE:
        (A) NAME/KEY: N-linked glycosylation
        (B) LOCATION: 173 to 175
        (C) IDENTIFICATION METHOD: similarity with known
            sequence (ix) FEATURE:
        (A) NAME/KEY: N-linked glycosylation
        (B) LOCATION: 177 to 179
        (C) IDENTIFICATION METHOD: similarity with known
            sequence (ix) FEATURE:

(A) NAME/KEY: N-linked glycosylation
        (B) LOCATION: 192 to 194
        (C) IDENTIFICATION METHOD: similarity with known
            sequence (ix) FEATURE:
        (A) NAME/KEY: N-linked glycosylation
        (B) LOCATION: 198 to 200
        (C) IDENTIFICATION METHOD: similarity with known
            sequence (ix) FEATURE:
        (A) NAME/KEY: Ig V-set domain
        (B) LOCATION: 1 to 104
        (C) IDENTIFICATION METHOD: similarity with known
            sequence (ix) FEATURE:
        (A) NAME/KEY: Ig C-set domain
        (B) LOCATION:  105 to 202
        (C) IDENTIFICATION METHOD: similarity with known
            sequence (x) PUBLICATION INFORMATION:
        (A) AUTHORS: FREEMAN, GORDON J.
            FREEDMAN, ARNOLD S.
            SEGIL, JEFFREY M.
            LEE, GRACE
            WHITMAN, JAMES F.
            NADLER, LEE M.
        (B) TITLE: B7, A New Member Of The Ig Superfamily With
            Unique Expression On Activated And Neoplastic B Cells
        (C) JOURNAL: The Journal of Immunology
        (D) VOLUME: 143
        (E) ISSUE: 8
        (F) PAGES: 2714-2722
        (G) DATE:  15-OCT-1989
        (H) RELEVANT RESIDUES IN SEQ ID NO:2: From -26 to 262

(xi) SEQUENCE DESCRIPTION: SEQ ID NO:2:

Met Gly His Thr Arg Arg Gln Gly Thr Ser Pro Ser Lys Cys Pro Tyr
              -30              -25              -20

Leu Asn Phe Phe Gln Leu Leu Val Leu Ala Gly Leu Ser His Phe Cys
            -15              -10               -5

Ser Gly Val Ile His Val Thr Lys Glu Val Lys Glu Val Ala Thr Leu
   -1    1              5                 10

Ser Cys Gly His Asn Val Ser Val Glu Glu Leu Ala Gln Thr Arg Ile
 15              20              25              30

Tyr Trp Gln Lys Glu Lys Lys Met Val Leu Thr Met Met Ser Gly Asp
            35              40              45

Met Asn Ile Trp Pro Glu Tyr Lys Asn Arg Thr Ile Phe Asp Ile Thr
            50              55              60

Asn Asn Leu Ser Ile Val Ile Leu Ala Leu Arg Pro Ser Asp Glu Gly
            65              70              75

Thr Tyr Glu Cys Val Val Leu Lys Tyr Glu Lys Asp Ala Phe Lys Arg
 80              85              90

Glu His Leu Ala Glu Val Thr Leu Ser Val Lys Ala Asp Phe Pro Thr
 95              100             105             110

Pro Ser Ile Ser Asp Phe Glu Ile Pro Thr Ser Asn Ile Arg Arg Ile
            115             120             125

Ile Cys Ser Thr Ser Gly Gly Phe Pro Glu Pro His Leu Ser Trp Leu
            130             135             140

Glu Asn Gly Glu Glu Leu Asn Ala Ile Asn Thr Thr Val Ser Gln Asp
            145             150             155

Pro Glu Thr Glu Leu Tyr Ala Val Ser Ser Lys Leu Asp Phe Asn Met
 160             165             170

-continued

```
Thr Thr Asn His Ser Phe Met Cys Leu Ile Lys Tyr Gly His Leu Arg
175                 180                 185                 190

Val Asn Gln Thr Phe Asn Trp Asn Thr Thr Lys Gln Glu His Phe Pro
                195                 200                 205

Asp Asn Leu Leu Pro Ser Trp Ala Ile Thr Leu Ile Ser Val Asn Gly
            210                 215                 220

Ile Phe Val Ile Cys Cys Leu Thr Tyr Cys Phe Ala Pro Arg Cys Arg
        225                 230                 235

Glu Arg Arg Arg Asn Glu Arg Leu Arg Arg Glu Ser Val Arg Pro Val
240                 245                 250
```

(2) INFORMATION FOR SEQ ID NO:3:

(i) SEQUENCE CHARACTERISTICS:
        (A) LENGTH: 1716 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: no (vi) ORIGINAL SOURCE:
        (A) ORGANISM: Mus musculus
        (D) DEVELOPMENTAL STAGE: germ line
        (F) TISSUE TYPE: lymphoid
        (G) CELL TYPE: B lymphocyte
        (H) CELL LINE: 70Z and A20

(vii) IMMEDIATE SOURCE:
        (A) LIBRARY: cDNA in pCDM8 vector
        (B) CLONE: B7 #'s 1 and 29

(ix) FEATURE:
        (A) NAME/KEY: translated region
        (B) LOCATION: 249 to 1166 bp
        (C) IDENTIFICATION METHOD: similarity to other pattern (ix) FEATURE:
        (A) NAME/KEY: Alternate ATG initiation codons
        (B) LOCATION: 225 to 227 and 270 to 272
        (C) IDENTIFICATION METHOD: similarity to other pattern (xi) SEQUENCE DESCRIPTION: SEQ ID NO:3:

```
GAGTTTTATA CCTCAATAGA CTCTTACTAG TTTCTCTTTT TCAGGTTGTG AAACTCAACC      60

TTCAAAGACA CTCTGTTCCA TTTCTGTGGA CTAATAGGAT CATCTTTAGC ATCTGCCGGG     120

TGGATGCCAT CCAGGCTTCT TTTTCTACAT CTCTGTTTCT CGATTTTTGT GAGCCTAGGA     180

GGTGCCTAAG CTCCATTGGC TCTAGATTCC TGGCTTTCCC CATCATGTTC TCCAAAGCAT     240

CTGAAGCT ATG GCT TGC AAT TGT CAG TTG ATG CAG GAT ACA CCA CTC CTC      290
         Met Ala Cys Asn Cys Gln Leu Met Gln Asp Thr Pro Leu Leu
             -35                 -30                 -25

AAG TTT CCA TGT CCA AGG CTC AAT CTT CTC TTT GTG CTG CTG ATT CGT      338
Lys Phe Pro Cys Pro Arg Leu Asn Leu Leu Phe Val Leu Leu Ile Arg
            -20                 -15                 -10

CTT TCA CAA GTG TCT TCA GAT GTT GAT GAA CAA CTG TCC AAG TCA GTG      386
Leu Ser Gln Val Ser Ser Asp Val Asp Glu Gln Leu Ser Lys Ser Val
         -5                  -1  1                   5

AAA GAT AAG GTA TTG CTG CCT TGC CGT TAC AAC TCT CCT CAT GAA GAT      434
Lys Asp Lys Val Leu Leu Pro Cys Arg Tyr Asn Ser Pro His Glu Asp
 10                  15                  20                  25

GAG TCT GAA GAC CGA ATC TAC TGG CAA AAA CAT GAC AAA GTG GTG CTG      482
Glu Ser Glu Asp Arg Ile Tyr Trp Gln Lys His Asp Lys Val Val Leu
                 30                  35                  40
```

| | | |
|---|---|---|
| TCT GTC ATT GCT GGG AAA CTA AAA GTG TGG CCC GAG TAT AAG AAC CGG<br>Ser Val Ile Ala Gly Lys Leu Lys Val Trp Pro Glu Tyr Lys Asn Arg<br>45 50 55 | 530 | |
| ACT TTA TAT GAC AAC ACT ACC TAC TCT CTT ATC ATC CTG GGC CTG GTC<br>Thr Leu Tyr Asp Asn Thr Thr Tyr Ser Leu Ile Ile Leu Gly Leu Val<br>60 65 70 | 578 | |
| CTT TCA GAC CGG GGC ACA TAC AGC TGT GTC GTT CAA AAG AAG GAA AGA<br>Leu Ser Asp Arg Gly Thr Tyr Ser Cys Val Val Gln Lys Lys Glu Arg<br>75 80 85 | 626 | |
| GGA ACG TAT GAA GTT AAA CAC TTG GCT TTA GTA AAG TTG TCC ATC AAA<br>Gly Thr Tyr Glu Val Lys His Leu Ala Leu Val Lys Leu Ser Ile Lys<br>90 95 100 105 | 674 | |
| GCT GAC TTC TCT ACC CCC AAC ATA ACT GAG TCT GGA AAC CCA TCT GCA<br>Ala Asp Phe Ser Thr Pro Asn Ile Thr Glu Ser Gly Asn Pro Ser Ala<br>110 115 120 | 722 | |
| GAC ACT AAA AGG ATT ACC TGC TTT GCT TCC GGG GGT TTC CCA AAG CCT<br>Asp Thr Lys Arg Ile Thr Cys Phe Ala Ser Gly Gly Phe Pro Lys Pro<br>125 130 135 | 770 | |
| CGC TTC TCT TGG TTG GAA AAT GGA AGA GAA TTA CCT GGC ATC AAT ACG<br>Arg Phe Ser Trp Leu Glu Asn Gly Arg Glu Leu Pro Gly Ile Asn Thr<br>140 145 150 | 818 | |
| ACA ATT TCC CAG GAT CCT GAA TCT GAA TTG TAC ACC ATT AGT AGC CAA<br>Thr Ile Ser Gln Asp Pro Glu Ser Glu Leu Tyr Thr Ile Ser Ser Gln<br>155 160 165 | 866 | |
| CTA GAT TTC AAT ACG ACT CGC AAC CAC ACC ATT AAG TGT CTC ATT AAA<br>Leu Asp Phe Asn Thr Thr Arg Asn His Thr Ile Lys Cys Leu Ile Lys<br>170 175 180 185 | 914 | |
| TAT GGA GAT GCT CAC GTG TCA GAG GAC TTC ACC TGG GAA AAA CCC CCA<br>Tyr Gly Asp Ala His Val Ser Glu Asp Phe Thr Trp Glu Lys Pro Pro<br>190 195 200 | 962 | |
| GAA GAC CCT CCT GAT AGC AAG AAC ACA CTT GTG CTC TTT GGG GCA GGA<br>Glu Asp Pro Pro Asp Ser Lys Asn Thr Leu Val Leu Phe Gly Ala Gly<br>205 210 215 | 1010 | |
| TTC GGC GCA GTA ATA ACA GTC GTC GTC ATC GTT GTC ATC ATC AAA TGC<br>Phe Gly Ala Val Ile Thr Val Val Val Ile Val Val Ile Ile Lys Cys<br>220 225 230 | 1058 | |
| TTC TGT AAG CAC AGA AGC TGT TTC AGA AGA AAT GAG GCA AGC AGA GAA<br>Phe Cys Lys His Arg Ser Cys Phe Arg Arg Asn Glu Ala Ser Arg Glu<br>235 240 245 | 1106 | |
| ACA AAC AAC AGC CTT ACC TTC GGG CCT GAA GAA GCA TTA GCT GAA CAG<br>Thr Asn Asn Ser Leu Thr Phe Gly Pro Glu Glu Ala Leu Ala Glu Gln<br>250 255 260 265 | 1154 | |
| ACC GTC TTC CTT TAGTTCTTCT CTGTCCATGT GGGATACATG GTATTATGTG<br>Thr Val Phe Leu | 1206 | |
| GCTCATGAGG TACAATCTTT CTTTCAGCAC CGTGCTAGCT GATCTTTCGG ACAACTTGAC | 1266 | |
| ACAAGATAGA GTTAACTGGG AAGAGAAAGC CTTGAATGAG GATTTCTTTC CATCAGGAAG | 1326 | |
| CTACGGGCAA GTTTGCTGGG CCTTTGATTG CTTGATGACT GAAGTGGAAA GGCTGAGCCC | 1386 | |
| ACTGTGGGTG GTGCTAGCCC TGGGCAGGGG CAGGTGACCC TGGGTGGTAT AAGAAAAAGA | 1446 | |
| GCTGTCACTA AAAGGAGAGG TGCCTAGTCT TACTGCAACT TGATATGTCA TGTTTGGTTG | 1506 | |
| GTGTCTGTGG GAGGCCTGCC CTTTTCTGAA GAGAAGTGGT GGGAGAGTGG ATGGGTGGG | 1566 | |
| GGCAGAGGAA AAGTGGGGGA GAGGGCCTGG GAGGAGAGGA GGGAGGGGGA CGGGGTGGGG | 1626 | |
| GTGGGGAAAA CTATGGTTGG GATGTAAAAA CGGATAATAA TATAAATATT AAATAAAAAG | 1686 | |
| AGAGTATTGA GCAAAAAAAA AAAAAAAAAA | 1716 | |

-continued (2) INFORMATION FOR SEQ ID NO:4:

(i) SEQUENCE CHARACTERISTICS:
        (A) LENGTH: 306 amino acids
        (B) TYPE: amino acid
        (C) TOPOLOGY: linear (ii) MOLECULE TYPE: protein
        (A) DESCRIPTION: B lymphocyte activation antigen; Ig
            superfamily member; T cell costimulatory signal
            via activation of CD28 pathways, binds to CD28+
            T cells, transmembrane protein (ix) FEATURE:
        (A) NAME/KEY: signal sequence
        (B) LOCATION: -37 to -1
        (C) IDENTIFICATION METHOD: similarity with known
            sequence
        (D) OTHER INFORMATION: hydrophobic (ix) FEATURE:
        (A) NAME/KEY: extracellular domain
        (B) LOCATION: 1 to 210
        (C) IDENTIFICATION METHOD: similarity with known
            sequence (ix) FEATURE:
        (A) NAME/KEY: transmembrane domain
        (B) LOCATION: 211 to 235
        (C) IDENTIFICATION METHOD: similarity with known
            sequence (ix) FEATURE:
        (A) NAME/KEY: intracellular (cytoplasmic) domain
        (B) LOCATION: 236 to 269
        (C) IDENTIFICATION METHOD: similarity with known
            sequence (ix) FEATURE:
        (A) NAME/KEY: Ig V-set domain
        (B) LOCATION: 1 to 105
        (C) IDENTIFICATION METHOD: similarity with known
            sequence (ix) FEATURE:
        (A) NAME/KEY: Ig C-set domain
        (B) LOCATION: 106 to 199
        (C) IDENTIFICATION METHOD: similarity with known
            sequence (x) PUBLICATION INFORMATION:
        (A) AUTHORS: FREEMAN, GORDON J.
            GRAY, GARY S.
            GIMMI, CLAUDE D.
            LOMBARD, DAVID B.
            ZHOU, LIANG-JI
            WHITE, MICHAEL
            FINGEROTH, JOYCE D.
            GRIBBEN, JOHN G.
            NADLER, LEE M.
        (B) TITLE: Structure, Expression, and T Cell Costimulatory
            Activity Of The Murine Homologue Of The Human B
            Lymphocyte Activation Antigen B7
        (C) JOURNAL: Journal of Experimental Medicine
        (D) VOLUME:
        (E) ISSUE:
        (F) PAGES:
        (G) DATE: IN PRESS
        (H) RELEVANT RESIDUES IN SEQ ID NO:4: From -37 to 269

(xi) SEQUENCE DESCRIPTION: SEQ ID NO:4:

Met Ala Cys Asn Cys Gln Leu Met Gln Asp Thr Pro Leu Leu Lys Phe
       -35                   -30                 -25

Pro Cys Pro Arg Leu Ile Leu Leu Phe Val Leu Leu Ile Arg Leu Ser
       -20                   -15                 -10

Gln Val Ser Ser Asp Val Asp Glu Gln Leu Ser Lys Ser Val Lys Asp

-continued

```
 -5              -1   1              5                   10
Lys Val Leu Leu Pro Cys Arg Tyr Asn Ser Pro His Glu Asp Glu Ser
            15                  20              25

Glu Asp Arg Ile Tyr Trp Gln Lys His Asp Lys Val Val Leu Ser Val
        30                  35              40

Ile Ala Gly Lys Leu Lys Val Trp Pro Glu Tyr Lys Asn Arg Thr Leu
        45              50                  55

Tyr Asp Asn Thr Thr Tyr Ser Leu Ile Ile Leu Gly Leu Val Leu Ser
60                  65              70                      75

Asp Arg Gly Thr Tyr Ser Cys Val Val Gln Lys Lys Glu Arg Gly Thr
                80                  85                  90

Tyr Gly Val Lys His Leu Ala Leu Val Lys Leu Ser Ile Lys Ala Asp
            95                  100             105

Phe Ser Thr Pro Asn Ile Thr Glu Ser Gly Asn Pro Ser Ala Asp Thr
            110             115             120

Lys Arg Ile Thr Cys Phe Ala Ser Gly Gly Phe Pro Lys Pro Arg Phe
        125             130             135

Ser Trp Leu Glu Asn Gly Arg Glu Leu Pro Gly Ile Asn Thr Thr Ile
140             145             150                     155

Ser Gln Asp Pro Glu Ser Glu Leu Tyr Thr Ile Ser Ser Gln Leu Asp
            160             165             170

Phe Asn Thr Thr Arg Asn His Thr Ile Lys Cys Leu Ile Lys Tyr Gly
            175             180             185

Asp Ala His Val Ser Glu Asp Phe Thr Trp Glu Lys Pro Pro Glu Asp
        190             195             200

Pro Pro Asp Ser Lys Asn Thr Leu Val Leu Phe Gly Ala Gly Phe Gly
    205             210             215

Ala Val Ile Thr Val Val Val Ile Val Val Ile Ile Lys Cys Phe Cys
220             225             230             235

Lys His Arg Ser Cys Phe Arg Arg Asn Glu Ala Ser Arg Glu Thr Asn
            240             245             250

Asn Ser Leu Thr Phe Gly Pro Glu Glu Ala Leu Ala Glu Gln Thr Val
            255             260             265

Phe Leu
```